US011340014B2

(12) United States Patent
Trout et al.

(10) Patent No.: US 11,340,014 B2
(45) Date of Patent: May 24, 2022

(54) FREEZE-DRYING METHODS AND RELATED PRODUCTS

(71) Applicants: Massachusetts Institute of Technology, Cambridge, MA (US); Politecnico di Torino, Turin (IT)

(72) Inventors: Bernhardt Levy Trout, Lexington, MA (US); Roberto Pisano, Rivalta di Torino (IT); Luigi Carlo Capozzi, Canosa di Puglia (IT)

(73) Assignees: Massachusetts Institute of Technology, Cambridge, MA (US); Politecnico di Torino, Turin (IT)

( * ) Notice: Subject to any disclaimer, the term of this patent is extended or adjusted under 35 U.S.C. 154(b) by 182 days.

(21) Appl. No.: 16/610,485

(22) PCT Filed: May 2, 2018

(86) PCT No.: PCT/US2018/030629
§ 371 (c)(1),
(2) Date: Nov. 1, 2019

(87) PCT Pub. No.: WO2018/204484
PCT Pub. Date: Nov. 8, 2018

(65) Prior Publication Data
US 2020/0158431 A1    May 21, 2020
US 2021/0180865 A9    Jun. 17, 2021

Related U.S. Application Data

(60) Provisional application No. 62/500,466, filed on May 2, 2017.

(51) Int. Cl.
*F26B 5/04* (2006.01)
*A23L 2/14* (2006.01)
(Continued)

(52) U.S. Cl.
CPC ............... *F26B 5/042* (2013.01); *A23L 2/14* (2013.01); *A61K 9/19* (2013.01); *F26B 5/048* (2013.01);
(Continued)

(58) Field of Classification Search
CPC .......... F26B 5/042; F26B 5/048; F26B 5/046; F26B 15/04; A23V 2002/00; A23L 2/14; A61K 9/19
(Continued)

(56) References Cited

U.S. PATENT DOCUMENTS 2,285,336 A    6/1942 Jackson et al.
3,192,645 A    7/1965 Oetjen et al.
(Continued)

FOREIGN PATENT DOCUMENTS

CN    204917150    12/2015
CN    105928327    9/2016
(Continued)

OTHER PUBLICATIONS

Bae et al., A numerical model for freeze drying processes with infrared radiation heating. Numerical Heat Transfer, Part A: Applications. 2010;58(5):333-355.
(Continued)

*Primary Examiner* — Stephen M Gravini
(74) *Attorney, Agent, or Firm* — Wolf, Greenfield & Sacks, P.C.

(57) ABSTRACT

The disclosure in some aspects relates to systems and related methods for the continuous freeze-drying of materials (e.g., pharmaceuticals) with high speed and control.

16 Claims, 36 Drawing Sheets

(51) Int. Cl.
*A61K 9/19* (2006.01)
*F26B 5/06* (2006.01)
*F26B 15/04* (2006.01)

(52) U.S. Cl.
CPC .............. *F26B 5/06* (2013.01); *F26B 15/04* (2013.01); *A23V 2002/00* (2013.01)

(58) Field of Classification Search
USPC .......................................................... 34/296
See application file for complete search history.

(56) References Cited

U.S. PATENT DOCUMENTS

| | | | |
|---|---|---|---|
| 3,203,108 | A | 8/1965 | Broadwin |
| 4,104,807 | A | 8/1978 | Braun |
| 5,723,508 | A | 3/1998 | Healy et al. |
| 5,964,043 | A * | 10/1999 | Oughton .................. F26B 5/06 34/92 |
| 9,796,273 | B2 * | 10/2017 | Ragazzini ................. F26B 5/06 |
| 10,139,160 | B2 * | 11/2018 | Fu ........................... F26B 5/041 |
| 10,578,359 | B2 * | 3/2020 | Durance ................. F26B 5/048 |
| 10,921,058 | B2 * | 2/2021 | Nguyen .................... F26B 5/06 |
| 11,047,620 | B2 * | 6/2021 | Beutler ................... F26B 21/14 |
| 11,054,185 | B1 * | 7/2021 | Trappier ................. A61J 1/165 |
| 11,067,336 | B2 * | 7/2021 | Corbin, III ............... A61L 2/10 |
| 2004/0053204 | A1 | 3/2004 | Morris et al. |
| 2014/0215845 | A1 | 8/2014 | Corver et al. |
| 2021/0055050 | A1 * | 2/2021 | Triglia, Jr. ............. F26B 13/008 |
| 2021/0180865 | A9 * | 6/2021 | Trout .................... F26B 25/003 |

FOREIGN PATENT DOCUMENTS

| | | | |
|---|---|---|---|
| WO | WO 1996/029556 | A1 | 9/1996 |
| WO | WO 2007/066132 | A1 | 6/2007 |
| WO | WO 2013/036107 | A2 | 3/2013 |
| WO | WO 2016/191799 | A1 | 12/2016 |
| WO | WO-2018204484 | A1 * | 11/2018 ............. F26B 5/048 |
| WO | WO-2019103731 | A1 * | 5/2019 ............. F26B 25/008 |

OTHER PUBLICATIONS

Barresi et al., Model-Based Monitoring and Control of Industrial Freeze-Drying Processes: Effect of Batch Nonuniformity. Drying Tech. 2010;28:577-590.

Capozzi et al., From batch to continuous: freeze-drying of suspended vials for pharmaceuticals in unit-doses. Industrial & Engineering Chemistry Research. 2019;58(4):1635-1649.

De Meyer et al., Evaluation of spin freezing versus conventional freezing as part of a continuous pharmaceutical freeze-drying concept for unit doses. Int J Pharm. 2015;496(1):75-85. doi:10.1016/j.ijpharm.2015.05.025.

Ganguly et al., Experimental determination of the key heat transfer mechanisms in pharmaceutical freeze-drying. J Pharm Sci. May 2013;102(5):1610-25. doi: 10.1002/jps.23514. Epub Mar. 26, 2013.

Kramer et al., Freeze-drying using vacuum-induced surface freezing. J Pharm Sci. Feb. 2002;91(2):433-43.

Kuu et al., Gap-freezing approach for shortening the lyophilization cycle time of pharmaceutical formulations—demonstration of the concept. J Pharm Sci. Aug. 2013;102(8):2572-88. doi: 10.1002/jps.23610. Epub May 31, 2013.

Oddone et al., Impact of vacuum-induced surface freezing on inter- and intra-vial heterogeneity. Eur J Pharm Biopharm. Jun. 2016;103:167-178. doi: 10.1016/j.ejpb.2016.04.002. Epub Apr. 5, 2016.

Oddone et al., Vacuum-induced nucleation as a method for freeze-drying cycle optimization. Industrial & Engineering Chemistry Research. 2014;53(47):18236-18244.

Pisano et al., Achieving continuous manufacturing in lyophilization: Technologies and approaches. Eur J Pharm Biopharm. Sep. 2019;142:265-279. doi: 10.1016/j.ejpb.2019.06.027. Epub Jun. 25, 2019.

Pisano et al., Heat transfer in freeze-drying apparatus. Heat Transfer. 2011;1:91-114.

Pisano et al., Prediction of product morphology of lyophilized drugs in the case of Vacuum Induced Surface Freezing. Chemical Engineering Research and Design. 2017;125: 119-129.

Rambhatla et al., Heat and mass transfer scale-up issues during freeze-drying, I: atypical radiation and the edge vial effect. Aaps Pharmscitech. 2003;4(2):22-31.

Van Bockstal et al., Noncontact Infrared-Mediated Heat Transfer During Continuous Freeze-Drying of Unit Doses. J Pharm Sci. Jan. 2017;106(1):71-82. doi: 10.1016/j.xphs.2016.05.003. Epub Jun. 16, 2016.

PCT/US2018/030629, Jul. 3, 2018, Invitation to Pay Additional Fees.

PCT/US2018/030629, Sep. 7, 2018, International Search Report and Written Opinion.

PCT/US2018/030629, Nov. 14, 2019, International Preliminary Report on Patentability.

[No Author Listed] Aseptic processing and freeze drying solutions. IMALIFE. Nov. 2015.

[No Author Listed] Production Freeze Dryers. Retrieved at http://en.tofflon.com/menu/production-freeze-dryers.html. Apr. 5, 2015.

Barresi et al., Monitoring of the primary drying of a lyophilization process in vials. Chem Eng Process: Process Intens. Jan. 2009;48(1):408-423.

De Meyer et al., Evaluation of spin freezing versus conventional freezing as part of a continuous pharmaceutical freeze-drying concept for unit doses. Int J Pharm. Dec. 30, 2015;496(1):75-85. doi: 10.1016/j.ijpharm.2015.05.025. Epub May 14, 2015.

Emteborg et al., Infrared thermography for monitoring of freeze-drying processes: instrumental developments and preliminary results. J Pharm Sci. Jul. 2014;103(7):2088-2097. doi: 10.1002/jps.24017. Epub Jun. 5, 2014.

EP 18794019.2, Mar. 12, 2021, Extended European Search Report.

* cited by examiner

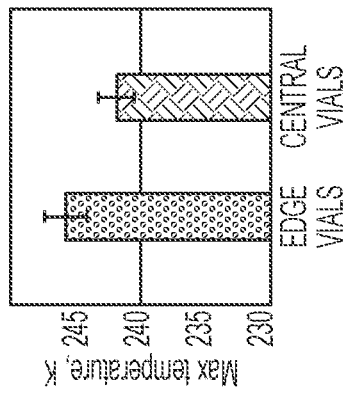
FIG. 17C
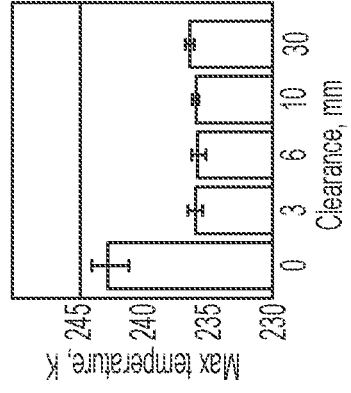
FIG. 17F
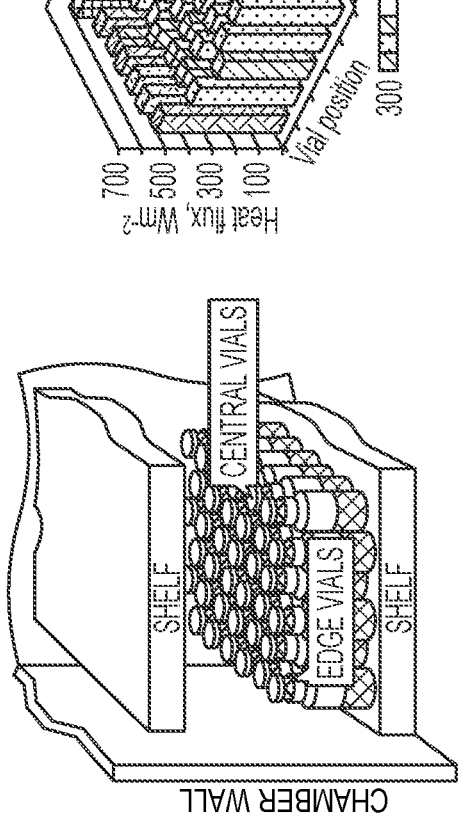
FIG. 17B
FIG. 17A
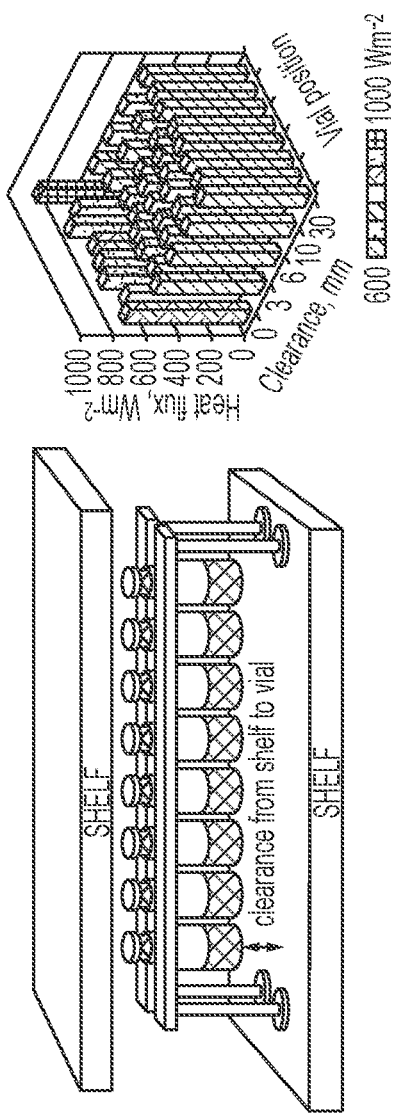
FIG. 17E
FIG. 17D

FREEZE-DRYING METHODS AND RELATED PRODUCTS

RELATED APPLICATIONS

This application is a national stage filing under 35 U.S.C. 371 of International Patent Application Serial No. PCT/US2018/030629, filed May 2, 2018, entitled "FREEZE-DRYING METHODS AND RELATED PRODUCTS", which claims the benefit of priority under 35 U.S.C. § 119(e) to U.S. Provisional Patent Application Ser. No. 62/500,466, filed May 2, 2017, and entitled "CONTINUOUS FREEZE-DRYING METHODS AND RELATED PRODUCTS," each of which is incorporated herein by reference in its entirety for all purposes.

FIELD

The present disclosure relates to methods for the freeze-drying of substances, e.g., pharmaceuticals and biopharmaceuticals in unit doses, and related products and apparatus. This technology is also suitable for processing other kinds of products, e.g., fruit pulps and juices. The disclosure also includes lyophilized products produced using this process.

BACKGROUND

It is desirable to freeze-dry substances, for example, to preserve biological activity in the case of pharmaceuticals. Freeze-drying, or lyophilization, is a technique that is often used for drying high-value products without damaging their physical structure and/or preserving the stability of the product during long storage. For example, many pharmaceuticals and biopharmaceuticals are delicate and unstable in liquid solution, and are also heat-sensitive. Therefore, certain methods cannot be used to dry these materials and freeze-drying is a potential solution. Improved methods for freeze-drying are needed.

SUMMARY

The present disclosure relates to methods for the freeze-drying of substances, e.g., pharmaceuticals and biopharmaceuticals in unit doses, and related products and apparatus. This technology is also suitable for processing other kinds of products, e.g., fruit pulps and juices. The disclosure also includes lyophilized products produced using this process.

In some aspects, the present disclosure provides methods for processing a composition.

In some embodiments, a method comprises continuously moving a vessel, configured to contain a composition, through a plurality of modules arranged to promote step-wise freezing and/or drying of the composition, wherein the vessel comprises a housing defining a boundary between an exterior surrounding of the vessel and an interior space configured to contain the composition, and wherein, during movement of the vessel through the plurality of modules, the vessel is arranged to promote heat transfer (e.g., substantially uniform heat transfer) between the exterior surrounding and the interior space across a portion of the housing contactable with the composition in the interior space when the composition is present in the interior space.

In other aspects, the present disclosure provides methods for freeze-drying a substance. In some embodiments, a method comprises: a) continuously moving a vessel that contains a composition comprising a substance through a conditioning module, wherein the vessel resides in the conditioning module for a time sufficient to bring the composition to a conditioning temperature; b) continuously moving the vessel from the conditioning module to, and then through, a freezing module, wherein the vessel resides in the freezing module for a time sufficient to freeze the composition; c) continuously moving the vessel from the freezing module to, and then through, a primary drying module, wherein the vessel resides in the primary drying module for a time sufficient to sublimate a frozen solvent from the composition; and in some embodiments d) continuously moving the vessel from the primary drying module to, and then through, a secondary drying module, wherein the vessel resides in the secondary drying module for a time sufficient to desorb residual solvent from the substance.

In some embodiments, a method comprises continuously moving a plurality of vessels along a common path and at a common rate through a plurality of modules arranged to promote step-wise freezing and/or drying of the composition, wherein each vessel is configured to contain the composition, wherein each vessel comprises a housing defining a boundary between an exterior surrounding of the vessel and an interior space configured to contain the composition.

According to some aspects, the present disclosure also provides systems for processing a composition. In some embodiments, a system comprises a plurality of modules arranged to promote step-wise freezing and drying of a composition; and a conveyer system configured to continuously move a vessel, configured to contain the composition, through the plurality of modules, wherein the vessel comprises a housing defining a boundary between an exterior surrounding of the vessel and an interior space configured to contain the composition, and wherein, when present in a module of the plurality of modules, the vessel is arranged to promote heat transfer (e.g., substantially uniform heat transfer) between the exterior surrounding and the interior space across the entire portion of the housing contactable with the composition in the interior space when the composition is present in the interior space.

In other aspects, the present disclosure also provides systems for the continuous freeze-drying of a composition. In some embodiments, a system comprises a first module and a second module, wherein the first module comprises a freezing chamber and the second module comprises a drying chamber, and wherein vessels comprising a composition are suspended in a line along a conveyor; and an interface apparatus connecting the first module to the second module.

Other advantages and novel features of the present disclosure will become apparent from the following detailed description of various non-limiting embodiments of the disclosure when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures:

FIG. 17A-FIG. 17F show a non-limiting comparison of heat flux between batch freeze-drying and continuous freeze-drying; FIG. 17A shows a schematic of vial positions in a non-limiting case of a batch lyophilizer; FIG. 17B shows a spatial distribution of heat flux in a non-limiting case of a batch lyophilizer; FIG. 17C shows a maximum product temperature for vessels placed at the edge and in center of a shelf in a non-limiting case of a batch lyophilizer; FIG. 17D shows a schematic of vessels arrangement in a non-limiting case of a continuous lyophilizer (i.e., freeze-dryer); FIG. 17E shows a spatial distribution of heat flux in a non-limiting case of a continuous lyophilizer; and FIG. 17F shows the maximum product temperature of products as a function of clearance in a non-limiting case of a continuous lyophilizer;

DETAILED DESCRIPTION

Figure 1:
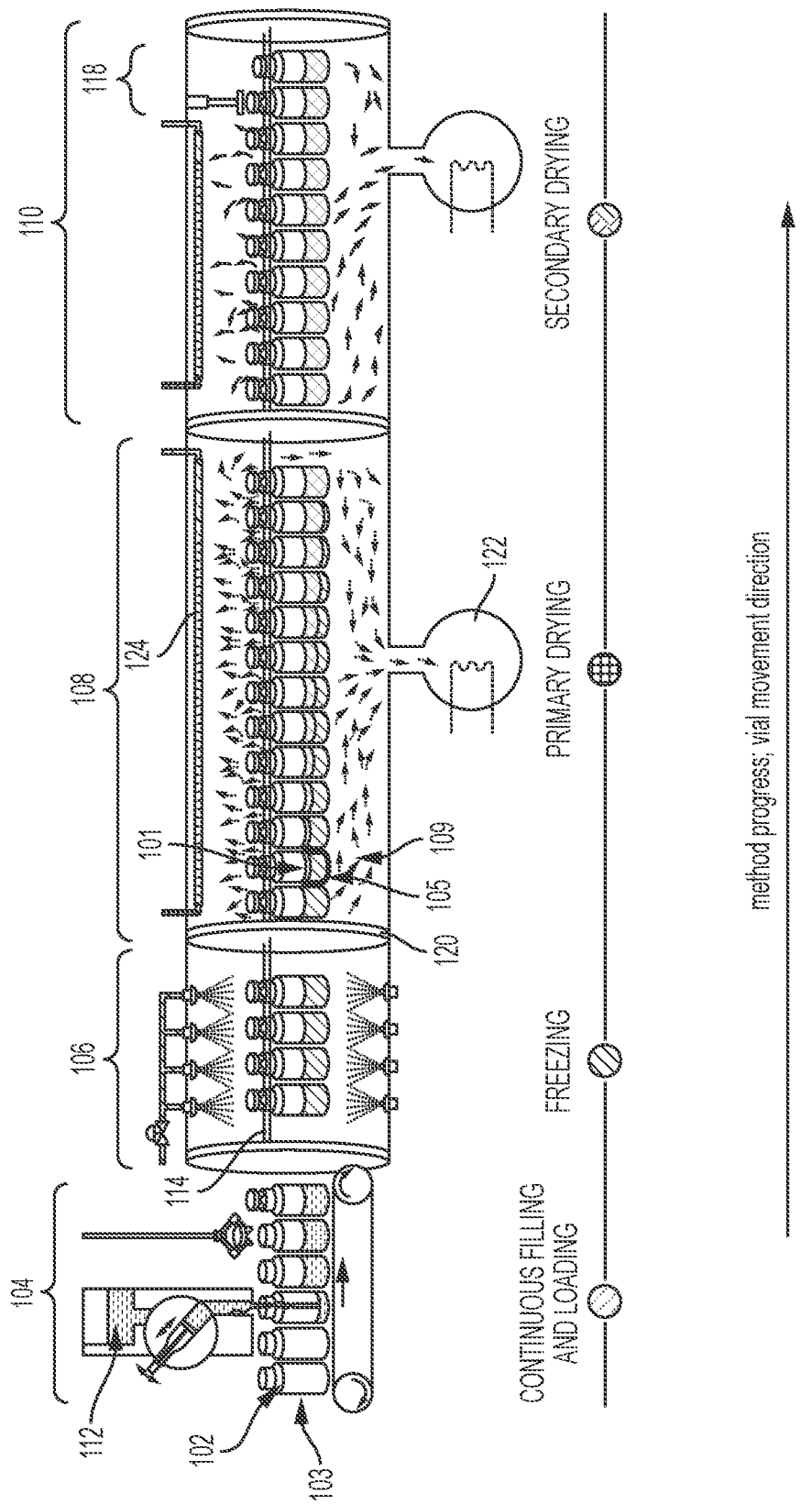
FIG. 1 provides a non-limiting schematic diagram of a continuous freeze-drying process for liquid solutions comprising: (1) moving tracks, (2) sluice-gate/load-lock system, (3) condenser and vacuum pumps, and (4) temperature controlled surfaces.

The disclosure in some aspects relates to systems and related methods for the continuous freeze-drying of materials (e.g., pharmaceuticals) with high speed and control. Aspects of the disclosure relate to recognizing deficiencies in conventional batch freeze-drying, a downstream process in the pharmaceutical industry used to gently dry high-value products which are sensitive to heat. In some cases, batch freeze-drying is a relatively long and expensive process that presents serious limitations.

A batch lyophilizer may comprise a chamber equipped with shelves and connected to a condenser and vacuum pumps. Shelves may be designed to freeze and to heat the product through internal channels, allowing circulation of silicone oil or an equivalent fluid. The silicone oil may be cooled down or heated by a cooling/heating system.

Batch freeze-drying may comprise three stages: (a) freezing the liquid solution in a container (e.g. a vessel; e.g. a vial), (b) drying the material by removing water via sublimation under vacuum, and (c) removing residual moisture via desorption under vacuum. As a first step, vessels may be loaded over the shelves into the chamber. In the freezing step, the shelf temperature may be reduced until product in vessels is completely frozen. After freezing, the pressure in the chamber may be reduced, causing sublimation of ice. Finally, the shelf temperature may be increased, causing desorption of residual moisture in the products.

More specifically, the batch freeze-drying process may comprise various stages: (1) filling and loading of the material, (2) freezing, (3) primary drying, (4) secondary drying, (5) backfill and stoppering, (6) unloading of the material, (7) defrosting of condenser, (8) cleaning in place, (9) sterilization in place, (10) further sterilization with $H_2O_2$, (11) leak test.

The whole batch freeze-drying process can take from 40 to 300 hours, and more than 50% of this time is dead time (e.g., stages 1, 5, 6, 7, 8, 9, 10, and 11).

Issues related to batch freeze-drying may include: lack of flexibility of processing; large apparatus volume required to process the product; long dead time for loading/unloading and cleaning/sterilizing; safety issues related to manual handling, product contamination, and operator contamination; technical issues related to breakdown of components and failure to obtain the desired pressure reduction, due to pump breakdown or leaks in the apparatus; non-uniformity of the products; non-uniform heat/mass transfer during the process; lack of control during the process; and/or difficulties in the scale-up of the process.

Certain embodiments of the present disclosure may overcome issues associated with batch freeze-drying related to ancillary operation by shortening the cycle time. In some embodiments, the present disclosure eliminates or minimizes the dead time of batch freeze-drying. Dead time may arise from for example filling and/or loading (about 5 hours), backfill and/or stoppering (about 1 hour), unloading (about 5 hours), cleaning in place, sterilization in place and further sterilization with $H_2O_2$ (5 to 10 hours) and leak test (3 to 6 hours).

Freezing often plays role in the lyophilization of pharmaceuticals because it may influence the final structure of the dried product, affect the composition of polymorphs and the stability of many drugs, and influence the duration of the drying stage and the final moisture content in the dried product. Moreover, freezing may influence the intra-vessel and the vessel-to-vessel heterogeneity. For example, in batch freeze-drying of pharmaceuticals, vessels may be filled with the liquid solution and then placed directly on the shelf of the freeze-drier. Once the vessels are loaded in the chamber, the shelf temperature may be reduced to below freezing temperature following a freezing protocol.

In batch freezing, some mechanisms involved in the heat transfer between the refrigerant fluid and the product in the vessel may be the conduction through air in the gap between the vessel and the shelf, radiation from the shelf and the surroundings, the contact between shelf and vessel, and the natural convection of air over the vessel side. During batch freezing, the product temperature may be an intermediate value between the temperature of the shelf and the air in the chamber. During batch freezing, the shelf may cool down the product temperature from the bottom, whereas the air in the chamber may supply heat to the side of the vessel. This may lead to temperature gradients within the product of between or equal to 4 degrees Celsius (° C.) and 5° C. and resultant heterogeneity in the structure of the dried product.

During a primary drying stage of conventional batch freeze-drying, variables to be controlled may include product temperature and drying time. Product temperature may be maintained below a limit value to satisfy the product quality requirements, while drying time may be long enough to ensure that ice sublimation is completed in all the vessels of the batch. The process parameters that can be directly controlled during primary drying may be shelf temperature and chamber pressure.

In conventional batch freeze-drying, vessels may be in direct contact with the shelves and occupy different positions over the shelf. The heat flux between the heating shelf and the vessels may be the result of various mechanisms that depend on dryer and vessel geometry, as well as on pressure and temperature of the shelves and the surroundings. In conventional batch freeze-drying, heat may be supplied by, for example, (i) direct conduction from the shelf to the glass at the points of contact, (ii) conduction through the gas in the small gap between the shelves and the bottom of the vessel, (iii) radiation from the bottom and upper shelf, and from the surroundings (i.e., chamber walls and door), and (iv) the natural convection of air over the vessel side. The heat supplied by direct contact and the heat supplied by radiation may be independent of chamber pressure, whereas convection and conduction may depend also on pressure.

Aspects of the disclosure relate to a recognition that heterogeneity in heat transfer may arise due to vessel-to-vessel variability of the contact surface between a shelf and a vessel; and vessel-to-vessel variability of gap distance between a shelf and a vessel bottom. Furthermore, the radiative contribution may depend on the position of the vessel in relation to a shelf or other support structure, e.g. vessels located in the center of the shelf receive radiative heat from bottom and upper shelves, vessels located in the periphery of the shelf receive also radiative heat from chamber walls or door, etc. This may present challenges for scaling-up of the process and in the process control itself. Other issues giving rise to heat transfer heterogeneity in the context of batch processes may include for example variability in shelf temperature (e.g., shelf temperature varies by between or equal to 1° C. and 3° C. along the shelf) and non-uniformity of pressure in the lyophilizer chamber, which may result in variation in drying rate and temperature within the lot during drying. Non-uniformity of pressure in a lyophilizer chamber may occur for manufacturing units working under full-load conditions. Under full-load conditions, pressure may vary from 1 Pa to 2 Pa or higher, from the center of a shelf to an edge of the shelf (see, e.g., Barresi et al. 2010, Drying Technology 28: 577-590).

Accordingly, in some embodiments, it is an object of the present disclosure to obviate or reduce the disadvantages of batch freeze-drying. In some embodiments, it is an object of the present disclosure to provide a lyophilization apparatus having one or more of the following features: a smaller apparatus that needs less space than conventional freeze-drier; no manual intervention during the whole process so as to avoid contamination of the product and operators; reduced cycle time and no dead time; increased homogeneity within the production and the standardization of the products; increased energy efficiency of the process; no need to scale up the process; and increased flexibility, resulting in complete integration with a given upstream process and modularity of the apparatus. In some embodiments, the present disclosure decreases drying time (e.g., by a factor of from 2 to 10, e.g., by a factor of from 2 to 5) over a conventional batch process.

In some embodiments, the present disclosure provides systems and related methods for continuous freeze-drying of pharmaceuticals and biopharmaceuticals in unit dose. In some embodiments, the present disclosure provides a unit dose continuous lyophilizer. In some embodiments, this system and related methods can be used with slurries, pulps, juice, or any fluid comprising any suitable target product to be freeze-dried in small vessels.

In some embodiments, advantages to the system and associated methods described herein include increased control and/or uniformity of heat supplied to products during primary and secondary drying. In some embodiments, systems and associated methods described herein minimize or eliminate edge-vessel effects because every vessel containing a composition to be freeze-dried follows approximately the same path and experiences approximately identical conditions. By contrast, an alternative method of freeze-drying developed for shortening cycle time, e.g., spin-freezing, may have less control over product structure.

Vessels containing compositions to be freeze-dried by methods described herein may have any suitable dimensions or filling volume, without limitation. By contrast, an alternative method of freeze-drying developed for shortening cycle time, e.g., spin-freezing, may be limited in filling volume and vessel dimensions.

In some embodiments, systems and methods described herein were designed to produce end-use products, and to avoid the drawbacks of batch lyophilization in vessels (e.g., vials). By contrast, alternative continuous lyophilization systems and methods may not produce end-use products, but rather may produce bulk materials in the form of fine particles which must be subsequently handled, which handling may reduce product quality. In addition, alternative continuous lyophilization systems and methods may have less control over product temperature and final moisture within the product.

In some embodiments, a system for processing a composition is provided. In some embodiments, a system provided herein comprises a plurality of modules (e.g., 104, 106, 108, 110 of FIG. 1) arranged to promote step-wise freezing and drying of a composition (e.g., 112 of FIG. 1), and a conveyer system (e.g., 114 of FIG. 1) configured to continuously move a vessel (e.g., 102 of FIG. 1), configured to contain the composition, through the plurality of modules. In some embodiments, a vessel (e.g., 102 of FIG. 1) comprises a housing (e.g., 103 of FIG. 1) defining a boundary between an exterior surrounding (e.g., 109 of FIG. 1) of the vessel and an interior space (e.g., 101 of FIG. 1) configured to contain the composition, and wherein, when present in a module (e.g., 106, 108, 110 of FIG. 1) of a plurality of modules, the vessel is arranged (e.g., using conveyor system 114 of FIG. 1) to promote heat transfer (e.g., substantially uniform heat transfer) between the exterior surrounding and the interior space across the entire portion (e.g., 105 of FIG. 1) of the housing contactable with the composition in the interior space when the composition is present in the interior space.

In some embodiments, a method for processing a composition is provided (e.g., as in FIG. 1). In some embodiments, a method provided herein comprises continuously moving a vessel (e.g., 102 of FIG. 1), configured to contain a composition (e.g., 112 of FIG. 1), through a plurality of modules (e.g., 104, 106, 108, 110 of FIG. 1) arranged to promote step-wise freezing and/or drying of the composition, wherein the vessel comprises a housing (e.g., 103 of FIG. 1) defining a boundary between an exterior surrounding (e.g., 109 of FIG. 1) of the vessel and an interior space (e.g., 101 of FIG. 1) configured to contain the composition, and wherein, during movement of the vessel (e.g., vial movement direction of FIG. 1) through the plurality of modules, the vessel is arranged (e.g., using conveyor system 114 of FIG. 1) to promote heat transfer (e.g., substantially uniform heat transfer) between the exterior surrounding and the interior space across a portion (e.g., 105 of FIG. 1) of the housing contactable with the composition in the interior space when the composition is present in the interior space.

Figure 12:
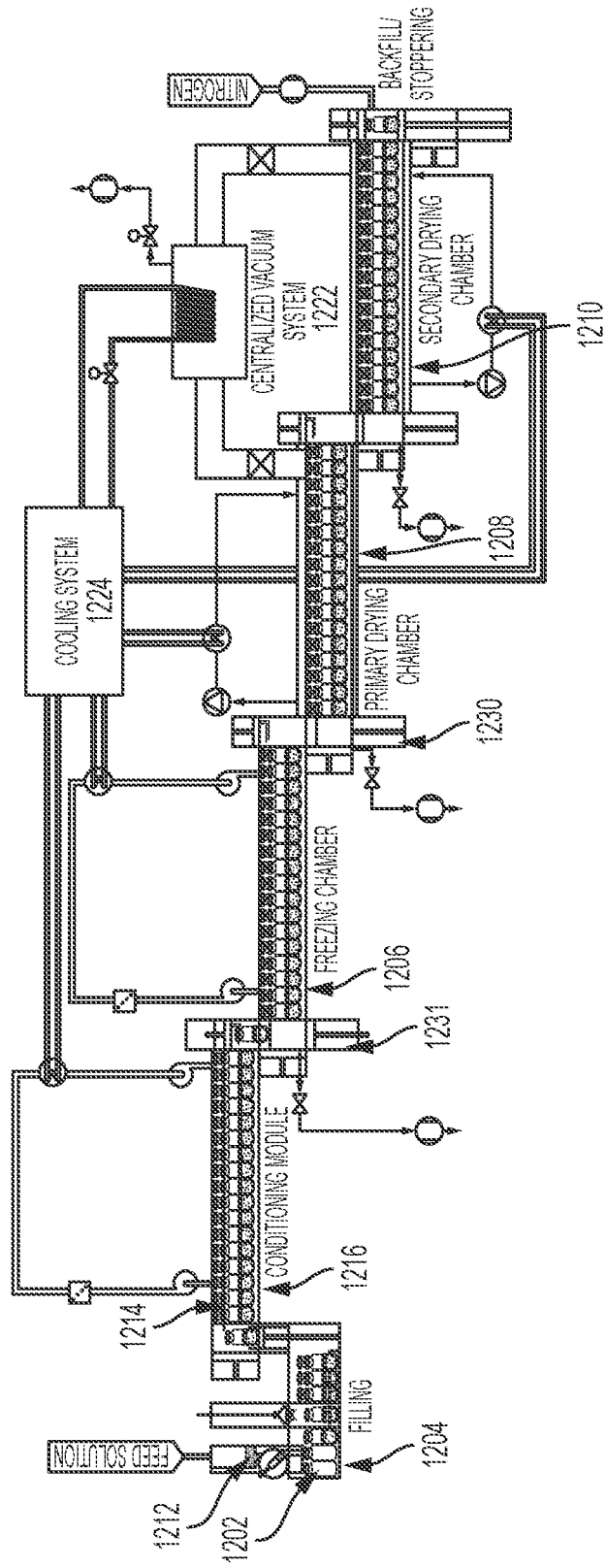
FIG. 12 depicts a non-limiting process flow diagram of a continuous freeze-dryer comprising: (A) conditioning module, (B) load-lock system, (C) freezing chamber, (D) primary drying chamber, and (D) secondary drying chamber.

In some embodiments, a system for the continuous freeze-drying of a composition is provided (e.g., FIG. 12). In some embodiments, a system provided herein comprises a first module (e.g., freezing module 1206 of FIG. 12) and a second module (e.g., primary drying module 1208 of FIG. 12) and an interface apparatus (e.g., load-lock system 1230 of FIG. 12) connecting the first module to the second module. In some embodiments, the first module comprises a freezing chamber and the second module comprises a drying chamber. In some embodiments, vessels (e.g., 1202 of FIG. 12) comprising a composition (e.g., 1212 of FIG. 12) are suspended in a line along a conveyor (e.g., 1214 of FIG. 12).

In some embodiments, a method for freeze-drying a substance is provided. In some embodiments, a method provided herein comprises a) continuously moving a vessel (e.g., 202 of FIG. 2) that contains a composition (e.g., 212 of FIG. 2) comprising a substance through a conditioning module (e.g., 216 of FIG. 2), wherein the vessel resides in the conditioning module for a time sufficient to bring the composition to a conditioning temperature; b) continuously moving the vessel from the conditioning module to, and then through, a freezing module (e.g., secondary freezing module 206 of FIG. 2), wherein the vessel resides in the freezing module for a time sufficient to freeze the composition; and c) continuously moving the vessel from the freezing module to, and then through, a primary drying module (e.g., 208 of FIG. 2), wherein the vessel resides in the primary drying module for a time sufficient to sublimate a frozen solvent from the composition.

In some embodiments, a system comprises a single module. In some embodiments, a system comprises a plurality of modules (e.g., one or more freezing modules and one or more drying modules). In some embodiments, two or more modules (e.g., some or all modules) are configured to work in parallel. In some embodiments, a system supports partial automation or full automation of a freeze-drying method. Systems provided herein may function under good manufacturing practices (GMP) conditions.

In some embodiments, a system comprises a filling module in which vessels (e.g., vials) are at least partially filled with a composition (e.g., comprising a target product) to be freeze-dried. In some embodiments, a filling module is configured for continuous filling of vessels. In some embodiments, filling involves at least partially filling one or more vessels with a composition to be freeze-dried. In some embodiments, filling comprises filling a vessel with a composition to between or equal to 1% and 90% volume capacity of the vessel (e.g., between or equal to 5% and 80% volume capacity, between or equal to 10% and 70% volume capacity, between or equal to 15% and 60% volume capacity, between or equal to 20% and 50% volume capacity, between or equal to 25% and 40% volume capacity, between or equal to 30% and 40% volume capacity). In some embodiments, a vessel is filled with a composition to between or equal to 10% and 50% volume capacity of the vessel. In some embodiments, a composition fills the vessel by less than half of the volume capacity of the vessel so as to prevent or diminish heterogeneous heat transfer resulting from contact between the vessel and conveying instrumentation (e.g., tracks) for the vessel. In some embodiments, a filling module is configured and operated to at least partially fill between or equal to 100 files per hour and 1000 vessels per hour (e.g., vials per hour) (e.g., between or equal to 200 vessels per hour and 900 vessels per hour, between or equal to 300 vessels per hour and 800 vessels per hour, between or equal to 300 vessels per hour and 100 vessels per hour, between or equal to 300 vessels per hour and 600 vessels per hour, 300 vessels per hour). In some embodiments, a system comprises a plurality of filling modules configured to function in parallel.

In some embodiments, a system provided herein comprises a conditioning module. In a conditioning module, flow of a cryogenic gas may cool down a vessel (e.g., vial), bringing a composition to a desired temperature. In some embodiments, a conditioning module is connected to a filling module. Methods described herein may involve moving a vessel from a filling module to a conditioning module. In some embodiments, a system comprises a plurality of conditioning modules configured to function in parallel.

In some embodiments, a system provided herein comprises a nucleation chamber, also referred to as a vacuum induced surface freezing (VISF) chamber. In a nucleation chamber, the pressure may be low enough to induce nucleation of solid crystals of a composition in the nucleation chamber. In some embodiments, a nucleation chamber is connected with a conditioning module. Methods described herein may involve moving a vessel from a conditioning module to a nucleation chamber. In some embodiments, a system comprises a plurality of nucleation chambers configured to function in parallel.

In some embodiments, a system provided herein comprises a freezing module. A system may comprise a plurality of freezing modules. In some embodiments, at least some freezing modules (e.g., all freezing modules) are connected to a refrigeration module (also herein referred to as a refrigeration system). In some embodiments, a system comprises 2 freezing modules, 3 freezing modules, 4 freezing modules, 5 freezing modules, 6 freezing modules, 7 freezing modules, 8 freezing modules, 9 freezing modules, 10 freezing modules, or another suitable number of freezing modules. In some embodiments, each freezing module is connected with a nucleation chamber (e.g., a respective nucleation chamber, a common nucleation chamber). In some embodiments, each freezing module is connected with a respective nucleation chamber. In some embodiments, each freezing module is connected with a common nucleation chamber. Methods described herein may involve moving a vessel from a nucleation chamber to a freezing module. In some embodiments, a system comprises a plurality of freezing modules configured to function in parallel.

In some embodiments, a system provided herein comprises a drying module. In some embodiments, a system comprises a plurality of drying modules. In some embodiments, a system comprises 2 drying modules, 3 drying modules, 4 drying modules, 5 drying modules, 6 drying modules, 7 drying modules, 8 drying modules, 9 drying modules, 10 drying modules, or another suitable number of drying modules. In certain embodiments, a system comprises 6 drying modules. In some embodiments, a system comprises a plurality of drying modules configured to function in parallel. In some embodiments, a system comprises a primary drying module and a secondary drying module configured in series. In some embodiments, a system comprises a plurality of drying module sets, each set comprising a primary drying module and a secondary drying module configured in series, wherein the drying module sets are configured to function in parallel.

In some embodiments, a freezing module in a system is connected to a plurality of drying modules. In some such embodiments, a freezing module directs one or more vessels (each containing a composition to be freeze-dried) to each drying module in a parallel configuration. In some embodiments, each vessel passes through a single freezing module and a single drying module during the freeze-drying process.

In some embodiments, a drying module or at least some drying modules (e.g., all drying modules) are connected to one or more refrigeration modules (also referred to herein as refrigeration systems). In some embodiments, at least some freezing modules and at least some drying modules are connected to a common refrigeration module or to respective refrigeration modules. In some embodiments, all drying modules are connected to a refrigeration system (e.g., a respective refrigeration system, a common refrigeration system). In some embodiments, all drying modules are connected to a comment refrigeration system. In some embodiments, all drying modules are connected to a respective refrigeration system.

In some embodiments, each drying module is connected to a vacuum system. In some embodiments, each drying module is connected to one or more condensers, each of which condensers is connected to one or more vacuum pumps. In some embodiments, a vacuum system comprises two vacuum pumps connected to two condensers; the two condensers in turn may be connected to each drying module. In some embodiments, a vacuum system comprises 3 vacuum pumps connected to 2 condensers; the two condenses in turn may be connected to each drying module. In some embodiments, a vacuum system comprises 3 vacuum pumps, with one vacuum pump for maintenance purposes. In certain illustrative embodiments, each condenser consumes between or equal to 1 kg of ice and 10 kg of ice per 72 hours, e.g., 4 kg of ice per 72 hours, 3.6 kg of ice per 72 hours. In certain illustrative embodiments, each condenser consumes between or equal to 1 kg of ice and 10 kg of ice per 12 hours, e.g., 4 kg of ice per 12 hours. In some embodiments, a system comprises a centralized vacuum system and a cooling system that distributes to each conditioning module, each freezing module, each primary drying module, and/or each secondary drying module. In some embodiments, a final drying module for a given series of modules (e.g., a secondary drying module) is connected to a backfill or stoppering module in which a product is sealed in a vessel. A backfill module or stoppering module may be connected to a source of nitrogen or other inert gas (e.g., Argon).

In some embodiments, throughput of a system (e.g., number of vessels per hour from composition to freeze-dried product) depends on a rate of advancement (movement) of vessels through the system. In some embodiments, each module has a fixed length. In some embodiments, throughput depends on length of some modules in a system. In some embodiments, throughput depends on the length of a path traveled by a vessel through some modules in a system. In some embodiments, throughput of a system depends on the rate of advancement of vessels and on the length of some modules. In some embodiments, where the rate of advancement of vessels is constant, the throughput of a system is determined by the number of modules working in parallel. In some embodiments, a system is configured and operated so as to freeze-dry compositions at a rate of between or equal to 10 vessels per hour per freezing module or drying module and 100 vessels per hour per freezing module or drying module (e.g., between or equal to 40 vessels per hour per module and 60 vessels per hour per module, 50 vessels per hour per module). In certain illustrative embodiments, a system is configured and operated so as to freeze-dry compositions at a rate of 300 vessels per hour. The throughput of freeze-dried vessels from a system may be 200,000 vessels per week. The throughput of freeze-dried vessels from a system may be two vessels per second.

In some embodiments, a system is arranged and operated such that one or more vessels containing a composition move through the system. In some embodiments, a system may be arranged and operated so as to continuously move a vessel containing a composition through a plurality of modules arranged to promote step-wise freezing and drying of the composition. In some embodiments, a system may be configured to continuously move a vessel containing a composition across a first module within the first module (intra-module movement), from the first module to the second module (module-to-module movement), and continuing along the remaining modules in continuous movement.

In some embodiments, a system comprises a load-lock system. In some embodiments, a system comprises one or more load-lock systems so that each vessel can move from a first module to a second module, e.g., in cases wherein the pressure condition of the first module is significantly different from the pressure condition of the second module. In some embodiments, a system comprises two load-lock systems for each module through which a vessel travels, one at an inlet to the module and one at an outlet to the module. A load-lock system may be located at an inlet for vessels (e.g., vials) to enter a module and/or an outlet for vessels (e.g., vials) to exit a module, e.g., to accommodate pressure changes between modules.

A vacuum duct may be configured to connect a freezing module or drying module to a condenser and/or vacuum pump. A freezing module or drying module may comprise a fluid inlet and a fluid outlet, e.g., through which a heat transfer fluid is flowed into and out of the freezing module or drying module, respectively. In some embodiments, a freezing module or drying module is configured for movement of a vessel (e.g., vial, e.g., 10R vial) through the freezing module or drying module and comprises a serpentine pattern, e.g., to compact the area occupied by the freezing module or drying module and to increase the length of the path traveled by a vessel moving through the freezing module or drying module (e.g., FIG. 33).

In some embodiments, a system provided herein includes one or more control systems for controlling one or more processing conditions, e.g., heat transfer fluid temperature, source temperature, and/or pressure. Non-limiting examples of control systems include one or more platinum resistance thermometers (PRTs), one or more pneumatic valves, or one or more pressure sensors, one or more wireless temperature sensors (one or more thermocouples), one or more cameras or laser sensors for in-line control of vacuum induced surface freezing (VISF), and/or one or more advanced control systems. In some embodiments, a system is configured for fully automated control of freeze-drying compositions in vessels. A system may be configured so as to employ process analytical technology (PAT), advanced control, scheduling, and/or other automated control systems and methods to control a temperature of a vessel (e.g., a temperature of a composition within the vessel) as it moves through a plurality of modules. A system may be configured so as to employ process analytical technology (PAT), advanced control, scheduling, and/or other automated control systems and methods to control a temperature of a composition within a vessel as the vessel moves through a plurality of modules.

In some embodiments, control of product quality is accomplished by precise control of the temperature of a composition being freeze-dried. In some embodiments, precise control involves maintaining the temperature of a composition being freeze-dried below a critical temperature above which the composition undergoes structural damage or denaturation of the active pharmaceutical ingredient. In some embodiments, maintaining the temperature of a composition below a critical temperature is accomplished by monitoring the temperature of the composition by wireless thermocouples and inputting measurements from the wireless thermocouples to a feedback control system that adjusts the temperature of a heat transfer fluid accordingly.

In some embodiments, a system comprises a model-based control system (also referred to herein as a feedback control system) for temperature regulation of a composition being freeze-dried. In some embodiments, a system includes wireless thermocouples for monitoring the temperature of a composition being freeze-dried. In some embodiments, measurements from wireless thermocouples, of the temperature of a composition being freeze-dried, are input into a model predictive controller (also referred to herein as a model-based control system) so as to adjust the temperature of a heat transfer fluid (or equivalently the temperature of a radiative surface within a freezing module or drying module in which the composition is located) and therefore so as to maintain the temperature of the composition at its desired value during freezing and/or drying, which may result in improved product quality.

A feedback control system for temperature of a composition being freeze-dried may be beneficial during a drying step, while a vessel containing the composition is in a drying module. By contrast, if a feedback control system is not employed, drying parameters including temperature, pressure, and time would likely be developed empirically by lyophilization professionals in a costly process, as is currently the case in some batch freeze-drying methods.

In some embodiments, a system includes one or more cleaning modules, one or more sterilization modules, and/or one or more cleaning/sterilization modules. In some embodiments, a common cleaning/sterilization module is connected to each freezing module and each drying module. In some embodiments, a respective cleaning/sterilization module is connected to each freezing module and each drying module. In some embodiments, a cleaning/sterilization module is operated to sterilize a freezing module or drying module, or to sterilize another module in a system provided herein, while the module is empty. In embodiments where a system provided herein comprises a plurality of freezing modules and a plurality of drying modules, a freeze-drying process may continue during sterilization of an empty freezing module or drying module. In some embodiments, sterilization of a freezing module or drying module is between or equal to 10 minutes and 2 hours in duration (e.g., between or equal to 30 minutes and one hour induration).

In some embodiments, the volume occupied by the one or more freezing modules and one or more drying modules of a system provided herein may be significantly less than the volume occupied by equipment used in batch freeze-drying for a similar number and volume of vessels containing compositions to be freeze-dried. In some embodiments, the volume occupied by the one or more freezing modules and one or more drying modules in a system provided herein is between or equal to 0.1 $m^3$ and 4 $m^3$ (e.g., between or equal to 0.1 $m^3$ and 0.3 $m^3$, between or equal to 0.15 $m^3$ and 0.25 $m^3$, 0.2 $m^3$, between or equal to 1 $m^3$ and 2 $m^3$, between or equal to 1.2 $m^3$ and 1.8 $m^3$, between or equal to 1.4 $m^3$ and 1.8 $m^3$, between or equal to 1.5 $m^3$ and 1.7 $m^3$, 1.6 $m^3$, 3 $m^3$, 2 $m^3$). In some embodiments, the volume occupied by an entire system provided herein is between or equal to 0.1 $m^3$ and 4 $m^3$ (e.g., between or equal to 1 $m^3$ and 3 $m^3$). In some embodiments, the volume occupied by an entire system provided herein is 2 $m^3$ or 3 $m^3$, whereas the volume of a comparable batch freeze-drying system may be 16 $m^3$. In some embodiments, the surface area occupied by each of the one or more freezing modules and one or more drying modules in a system provided herein is between or equal to 1 $m^2$ and 2 $m^2$ (e.g., between or equal to 1.2 $m^2$ and 1.7 $m^2$, 1.5 $m^2$). In some embodiments, one or more modules are stacked together. In certain illustrative embodiments, one or more freezing modules and one or more drying modules are stacked together. In certain illustrative embodiments, each of the one or more freezing modules and one or more drying modules in a system provided herein has a size of 1.2 m in length, 1.2 m in width, and 0.1 m in height. In certain illustrative embodiments, a stack of one or more freezing modules and one or more drying modules may be 1.2 m in length, 1.2 m in width, and 1.1 min height.

Figure 26:
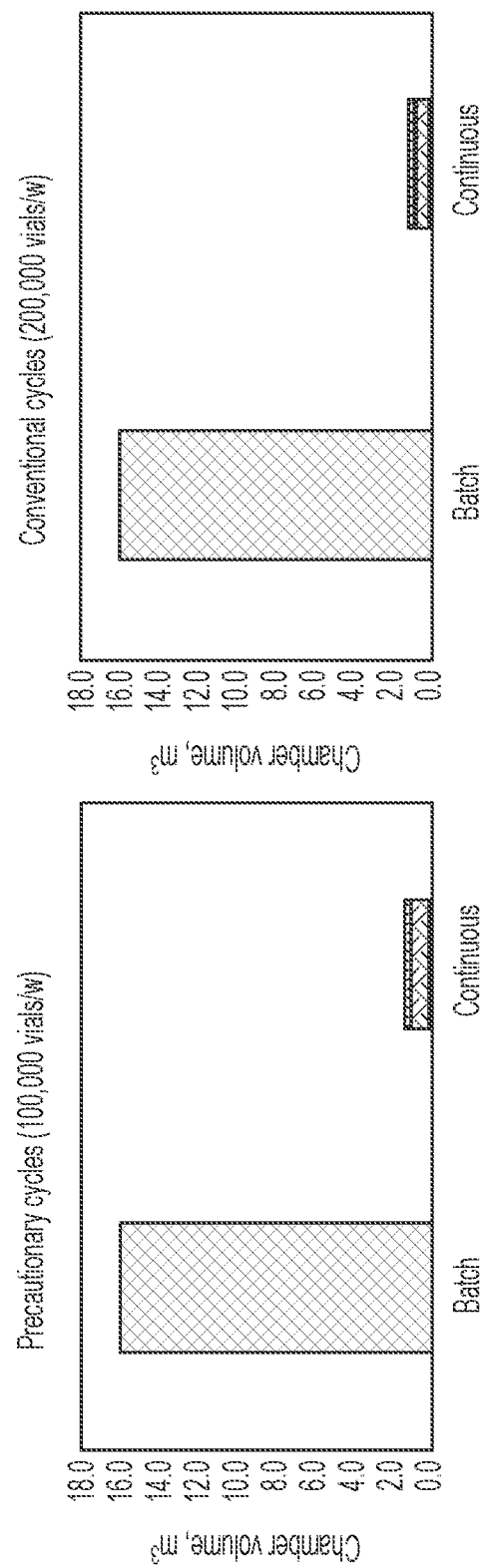
FIG. 26 shows non-limiting illustrative plots comparing equipment size for a batch lyophilizer and a continuous lyophilizer in the case of two different yields (left plot and right plot)
Figure 27:
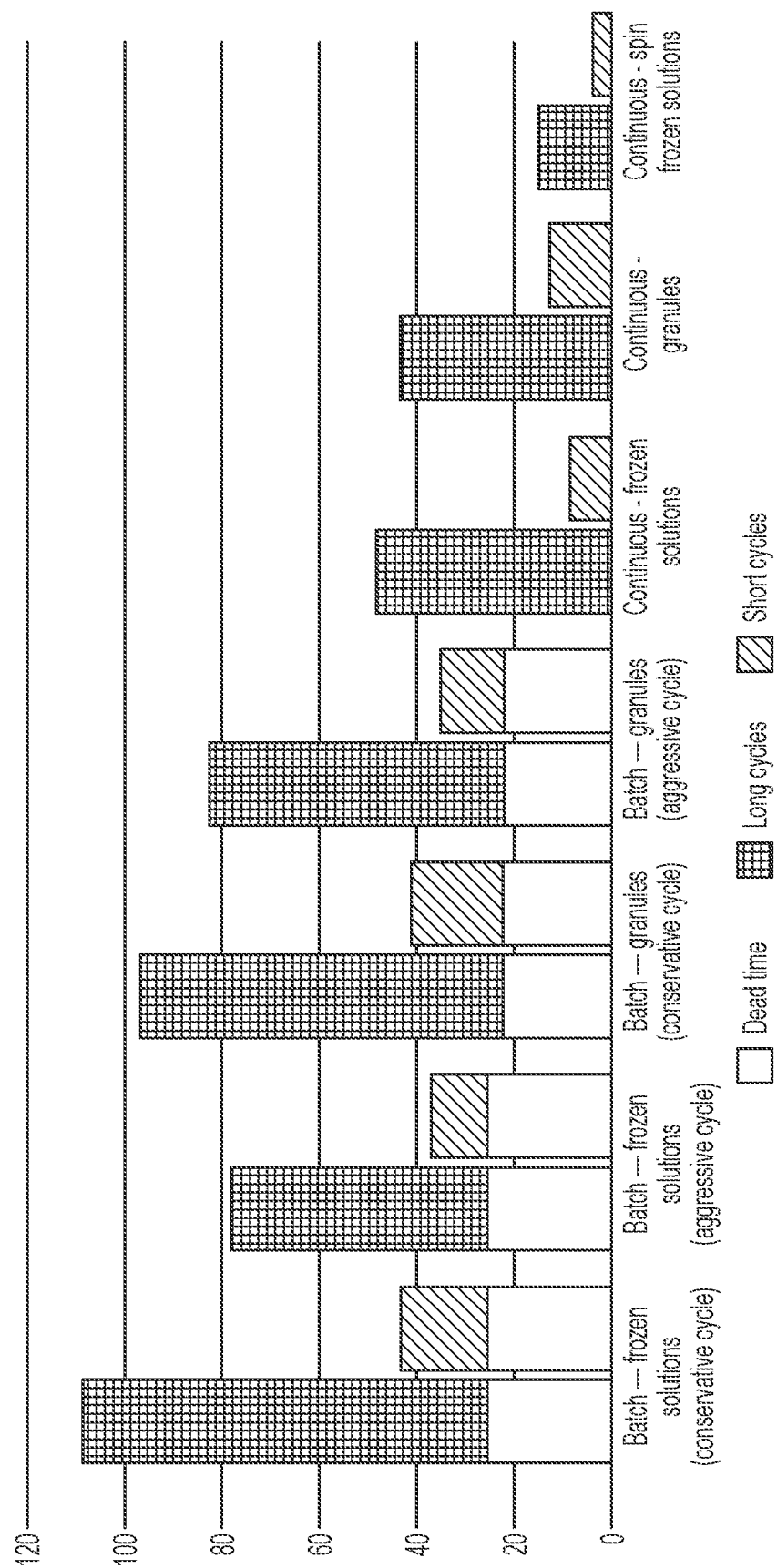
FIG. 27 shows a non-limiting illustrative plot comparing process time for a batch lyophilizer and a continuous lyophilizer.

In some embodiments, module volume in a system disclosed herein is 2, 3, 4, 5, 6, 7, 8, 9, 10, 11, or 12 times smaller than that of a module in a batch system (e.g., FIG. 26, precautionary cycles). In some embodiments, module volume in a system disclosed herein is 13, 14, or 15 times smaller than that of a module in a batch system (e.g., FIG. 26, conventional cycles).

In some embodiments, a system is operated to freeze-dry a pharmaceutical formulation. In some embodiments, freeze-drying occurs at least in part by vacuum induced surface freezing (VISF). In some embodiments, a pharmaceutical formulation comprises an excipient (e.g., sucrose, mannitol). An excipient may comprise a salt (e.g., sodium chloride). In some embodiments, a pharmaceutical formulation comprises an excipient at between or equal to 1 weight percent (wt %) and 10 weight percent versus the total weight of the pharmaceutical formulation (e.g., between or equal to 2 wt % and 8 wt %, between or equal to 3 wt % and 7 wt %, between or equal to 4 wt % and 6 wt %, 5 wt % versus the total weight of the pharmaceutical formulation). A composition to be freeze-dried may be a pharmaceutical formulation comprising 5 weight percent mannitol versus the total weight of the pharmaceutical formulation. In some embodiments, a pharmaceutical formulation comprises an active pharmaceutical ingredient (also referred to herein as a pharmaceutical; e.g., antidiuretic hormone (ADH)). An active pharmaceutical ingredient in a pharmaceutical formulation may be present in an amount such that a product of freeze-drying the pharmaceutical formulation comprises between or equal to 1 mg per gram and 10 mg per gram of the active pharmaceutical ingredient versus the total weight of the product. In a non-limiting certain illustrative embodiment, a pharmaceutical formulation comprises 5 weight percent sucrose versus the total weight of the pharmaceutical formulation and 0.05 weight percent ADH versus the total weight of the pharmaceutical formulation.

In some embodiments, a system is configured and operated so as to freeze-dry compositions at a rate of between or equal to 10 vessels per hour and 1000 vessels per hour. In some embodiments, a system is configured and operated to yield between or equal to 30 and 60 vessels per hour of freeze-dried product. In some embodiments, a system is configured and operated under conditions so as to produce between or equal to 10 vessels per hour and 1000 vessels per hour (e.g., between or equal to 40 vessels per hour and 60 vessels per hour, 50 vessels per hour, between or equal to 100 vessels per hour and 1000 vessels per hour, between or equal to 200 vessels per hour and 1000 vessels per hour, between or equal to 200 vessels per hour and 900 vessels per hour, between or equal to 200 vessels per hour and 800 vessels per hour, between or equal to 200 vessels per hour and 700 vessels per hour, between or equal to 200 vessels per hour and 600 vessels per hour, between or equal to 200 vessels per hour and 500 vessels per hour, between or equal to 200 vessels per hour and 400 vessels per hour, 300 vessels per hour).

The morphology (e.g., porosity, micro-porosity) of a product of freeze-drying may be defined by an excipient (e.g., sucrose, mannitol, lactose) rather than by an active pharmaceutical ingredient, e.g., in embodiments where the active pharmaceutical ingredient is present with the excipient in an amount between or equal to 1 mg of active pharmaceutical ingredient per gram of product and 10 mg of active pharmaceutical ingredient per gram of product.

In certain illustrative embodiments, a system comprises a filling module connected to a freezing module which is in turn connected to a drying module. In some such illustrative embodiments, both the freezing module and the drying module are connected to a refrigeration module, and the drying module is connected to two condensers which are in turn connected to vacuum pumps (e.g., FIG. 32).

In certain illustrative embodiments, a system comprises a continuous filling module connected to a freezing module, which is in turn connected to a plurality of drying modules. In some such illustrative embodiments, a refrigeration module is connected to both the freezing module and each of the plurality of drying modules. In some such embodiments, a cleaning/sterilization module is connected to both the freezing module and each of the plurality of drying modules. In some such embodiments, 3 vacuum pumps are connected to 2 condensers, which in turn are connected to each of the drying modules (e.g., FIG. 34).

In certain illustrative embodiments, a system includes one freezing module, 6 drying modules, 2 condensers, 3 vacuum pumps, 2 load-lock systems for each module, an automatic filling system, a cleaning/sterilization module, instrumentation for heat transfer fluid temperature control and pressure control (e.g., pneumatic valve, one or more pressure sensors, one or more platinum resistance thermometers), and automated control instrumentation (e.g., wireless temperature sensors, model-based controllers for selection of processing conditions for a composition of interest). In some such illustrative embodiments, the automatic filling system is connected to the freezing module, which is connected to each of the 6 drying modules so that the 6 drying modules are configured in parallel to one another, the load-lock systems connect the automatic filling system to the freezing module and/or connect the freezing module to each of the drying modules, the 3 vacuum pumps are connected to the 2 condensers which are connected to each of the 6 drying modules, a cleaning/sterilization module is connected to the freezing module and the 6 drying modules.

In some embodiments, non-limiting systems and associated methods for continuous lyophilization of pharmaceuticals in the form of unit-doses are provided. In some embodiments, a constant flow of vials may enter and leave a system provided herein, passing through different, specialized, chambers (e.g., FIG. 36).

In some embodiments, an apparatus (also referred to herein as a system) comprises a plurality of modules (e.g., a first module and a second module; e.g. a first chamber and a second chamber) in which vessels comprising target product flow along, experiencing different temperature and pressure conditions. In some embodiments, continuous flow is achieved by suspending vessels (e.g., vials) between two moving tracks (e.g., on a conveyor). In some embodiments, vessels are first continuously filled with a solution comprising target product and then move along modules having different conditions. A system, in some embodiments, comprises modules, each of which is dedicated to a single process step, that are connected each other to result in continuity of vessel flow and integration with downstream processes. In some embodiments, a first module is connected to a second module by an interface apparatus (e.g., a sluice-gate system, a load-lock system, a valve), so that each vessel can move from the first module to a second module in cases wherein the pressure condition of the first module is significantly different from the pressure condition of the second module.

In some embodiments, a module (e.g., comprising a chamber) may have a shape that is a cylinder, a rectangular prism, or any other suitable shape. In some embodiments, the walls of modules comprise stainless steel. In some embodiments, the walls of a given module have a relatively high emissivity coefficient (e.g., 0.85). In some embodiments, the temperature of the walls of a given module will be adjusted so as to regulate heat transfer from the equipment (e.g., walls) of the module to the product being freeze-dried, using known quantities such as the emissivity coefficient of the module walls.

In some embodiments, a system comprises three modules connected to one another in series: one freezing module and two drying modules. In such embodiments, it may be that in all three modules, vials are suspended and move continuously over a track. A freezing module may also be connected to a refrigeration system, that for example allows the introduction of flow of liquid nitrogen and regulation of flow rate of liquid nitrogen to cool vials as fast as possible. In some cases, a freezing module is configured to operate at atmospheric pressure, so it is not required to be connected to a vacuum system. Each drying module may be connected to a vacuum system.

By utilizing a configuration wherein vials are suspended, this may allow equipment-to-vial heat transfer to be very uniform. By contrast, a configuration used in conventional batch freeze-drying might require that vials are in direct contact with a temperature-controlled surface, promoting vial-to-vial variations in heat transfer due to variations in the geometry at the bottom of the vial. The gap at the bottom of vials may not be identical across vials, and even small variations can produce dramatic changes in heat transfer during freezing and/or during drying in batch processes. Vials that are commonly used in batch freeze-drying can also be used for continuous freeze-drying equipment. In some cases, if a maximum allowable product temperature is very low (e.g., below negative 30 degrees Celsius), external walls of vials may be coated with a polymeric film to reduce the emissivity of the vial material. A polymer film coating may allow for the use of a higher temperature of the equipment wall during drying, which would save energy for the refrigeration system.

In some embodiments, the condensing temperature of a solvent in a starting composition is greater than the minimum temperature reached by the surface of the condenser (e.g., negative 80 degrees Celsius). A condenser in some embodiments is a part of a vacuum system and is placed just before a vacuum pump to promote separation of condensable gases evacuated from the drying chambers.

In some embodiments, the length of a primary drying chamber is designed so as to provide a given productivity rate (e.g., number of vials per week) and facilitate appropriate residence time. As residence time may be product-specific, if a primary drying chamber is used for different types of product, it can be designed for a product that requires a long residence time, e.g., 48 h for primary drying. In some embodiments, primary drying is the bottle neck of a system provided herein, so primary drying determines the speed of travel of the vials. In some embodiments, for various productivity rates and cycle times, the speed of travel of vials is in the range of from 0.01 m/h to 2 m/h.

In some embodiments, modules may be configured in single file, e.g., linearly, and/or may be configured in parallel lines in order to increase productivity rate and flexibility (e.g., to respond to production variations).

In some embodiments, presently disclosed methods and systems exhibit one or more of the following advantages:
a) Reduced risk of contamination of products and operators;
b) No manual handling during a whole method;
c) Increased safety of the method;
d) Modular equipment and facilities increase flexibility and the productivity rate of the method;
e) Reduced inventory;
f) Reduced capital costs and reduced amount of partially processed materials;
g) Smaller ecological footprint;
h) Ready scale-up from laboratory to production units;
i) Continuous freeze-drying of different forms of products possible: bulk materials, spin-frozen materials, particle-based materials;
j) Continuous freeze-drying using different vessels possible: vials of desired dimension and material, syringes, double chamber cartridges, ampoule, phials (vials);
k) Improved product quality and standardization; and
l) In-line control of product quality.

In some embodiments, average pore size, in a composition being processed by system and method described herein, has an impact on both drying behavior and on preservation efficiency of biological activity of an active pharmaceutical ingredient in a product of freeze-drying. In some embodiments, the larger the pores are, the lower the resistance of the porous structure to vapor flow and hence the faster the drying. In some embodiments, the average pore size of product obtained from continuous freeze-drying systems and methods herein was greater than the average pore size of product obtained from batch freeze-drying systems and methods (e.g., FIG. 22, FIG. 31). It follows that in some embodiments, continuous freezing speeds up drying relative to batch freezing. Furthermore, in some embodiments, many active ingredients (e.g., active pharmaceutical ingredients) degrade because of adsorption over the solvent crystals surface (e.g., ice crystals surface). It follows that in some embodiments, the larger the pores are, the smaller the specific surface area of the product and the smaller the degradation of the active ingredients. Again, in some embodiments, systems and methods described herein for continuous freezing are beneficial to the efficiency of preservation of the active ingredients. In some embodiments, the average pore size of product obtained from continuous freeze-drying systems and methods herein is between or equal to 20 microns and 1000 microns, between or equal to 50 microns and 1000 microns, between or equal to 100 microns and 600 microns, between or equal to 100 microns and 400 microns, between or equal to 50 microns and 300 microns, between or equal to 50 microns and 200 microns, between or equal to 20 microns and 80 microns, between or equal to 40 microns and 70 microns, or between or equal to 100 microns and 200 microns. In certain embodiments, the average pore size of product obtained from continuous freeze-drying systems and methods herein was between or equal to 100 microns and 200 microns (e.g., FIG. 22, FIG. 31). Average pore size may be measured, e.g., by scanning electron microscopy. Turning to the figures, FIG. 1 shows a non-limiting illustrative schematic diagram of a continuous freeze-drying process and associated system for liquid solutions, slurries, pulps, juices, broth, foam, and any other suitable starting composition in vials.

A system provided in FIG. 1 comprises a plurality of modules comprising filling module 104, freezing module 106, primary drying module 108, and secondary drying module 110 arranged to promote step-wise freezing and drying of a composition 112, and a conveyer system 114 configured to continuously move a vessel 102, configured to contain the composition, through the plurality of modules. A vessel 102 in FIG. 1 comprises a housing 103 defining a boundary between an exterior surrounding 109 of the vessel and an interior space 101 configured to contain the composition, and wherein, when present in a module (e.g., 106, 108, 110) of a plurality of modules, the vessel is arranged (e.g., using conveyor system 114) to promote heat transfer (e.g., substantially uniform heat transfer) between the exterior surrounding and the interior space across the entire portion 105 of the housing contactable with the composition in the interior space when the composition is present in the interior space.

FIG. 1 also provides a schematic diagram for a non-limiting method for processing a composition. A non-limiting method as illustrated in FIG. 1 comprises continuously moving a vessel 102, configured to contain a composition 112, through a plurality of modules (e.g., 104, 106, 108, 110) arranged to promote step-wise freezing and/or drying of the composition, wherein the vessel comprises a housing 103 defining a boundary between an exterior surrounding 109 of the vessel and an interior space 101 configured to contain the composition, and wherein, during movement of the vessel (vial movement direction) through the plurality of modules, the vessel is arranged (e.g., using conveyor system 114) to promote heat transfer (e.g., substantially uniform heat transfer) between the exterior surrounding and the interior space across a portion 105 of the housing contactable with the composition in the interior space when the composition is present in the interior space.

The same concept can be applied for different vessels. In some embodiments, a process comprises the following steps:

a) a vessel 102 is continuously filled with a composition 112 in a sterile environment ("continuous filling") at filling module 104;
b) the vessel 102 is loaded into a conditioning module ("loading") and reaches the desired temperature (not shown);
c) the vessel 102 is moved into a freezing module 106 where it is cooled down by air convection until complete solidification occurs;
d) the vessel 102 is moved through an interface apparatus 120 into a primary drying module 108, where external pressure (using vacuum system 122) and temperature (using refrigeration system 124) are set to the values required to promote sublimation of ice from the frozen product;
e) the vessel 102 is moved into a secondary drying module 110, where external pressure and temperature are set to values in order to promote desorption of residual moisture from the dried product;
f) the vessel is moved into a pre-storage module 118, where the vessel is conditioned to storage temperature, backfilled with a proper inert gas and then closed.

Figure 2:
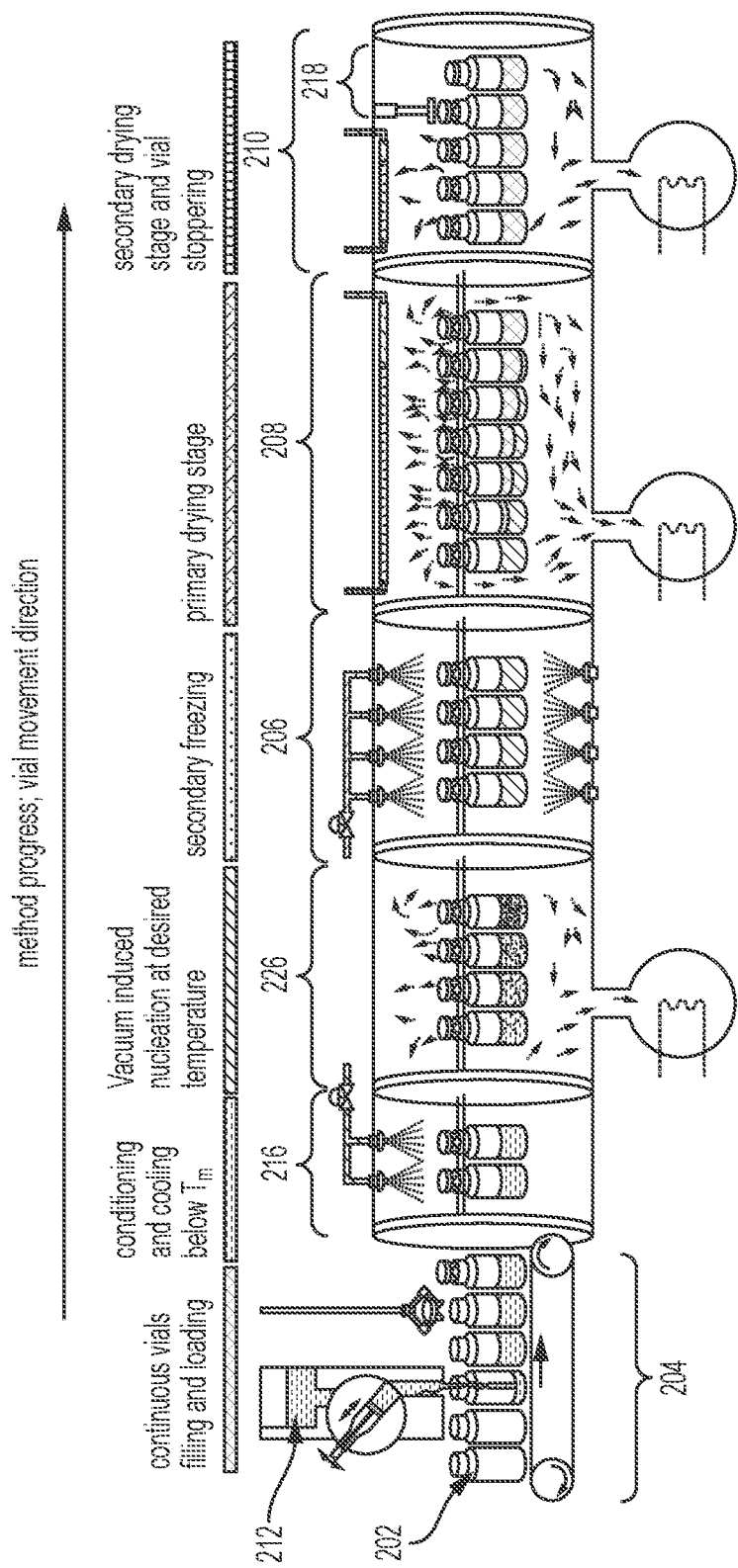
FIG. 2 provides a non-limiting schematic diagram of a continuous freeze-drying process for liquid solutions, which performs controlled nucleation through vacuum-induced surface freezing.

A non-limiting system and associated method for freeze-drying a substance is provided in FIG. 2. A non-limiting method as illustrated in FIG. 2 comprises a) continuously moving a vessel 202 that contains a composition 212 comprising a substance through a conditioning module 216, wherein the vessel resides in the conditioning module for a time sufficient to bring the composition to a conditioning temperature; b) continuously moving the vessel from the conditioning module to, and then through, a freezing module (e.g., secondary freezing module 206), wherein the vessel resides in the freezing module for a time sufficient to freeze the composition; and c) continuously moving the vessel from the freezing module to, and then through, a primary drying module 208, wherein the vessel resides in the primary drying module for a time sufficient to sublimate a frozen solvent from the composition.

FIG. 2 shows a non-limiting illustrative schematic diagram of a continuous freeze-drying process for liquid solutions, slurries, pulps, juices, broth, foam, and any other suitable starting composition in vials in which nucleation is induced through vacuum-induced surface freezing. The same concept can be applied for different vessels. The process comprises the following steps:

a) a vessel 202 is continuously filled in a sterile environment ("continuous vials filling and loading") at filling module 204;
b) the vessel is loaded into a conditioning module 216 ("conditioning and cooling below $T_m$" where $T_m$ is melting temperature of the composition) and reaches the temperature at which nucleation is desired;
c) the vessel is moved into a nucleation module 226, where the pressure is set to the desired pressure at the desired temperature and nucleation is induced in the product;
d) the vessel is moved into a secondary freezing module 206 where it is cooled down by air convection until complete solidification occurs;
e) the vessel is moved into a primary drying module 208, where the pressure and temperature are set to the values required to promote sublimation of ice from the frozen product;
f) the vessel is moved into a secondary drying module 210, where the pressure and temperature are set to the values required to promote desorption of residual moisture from the dried product;

g) the vessel is moved into the pre-storage module 218, where the vessel is conditioned to storage temperature, backfilled with a proper inert gas and then closed.

Figure 3:
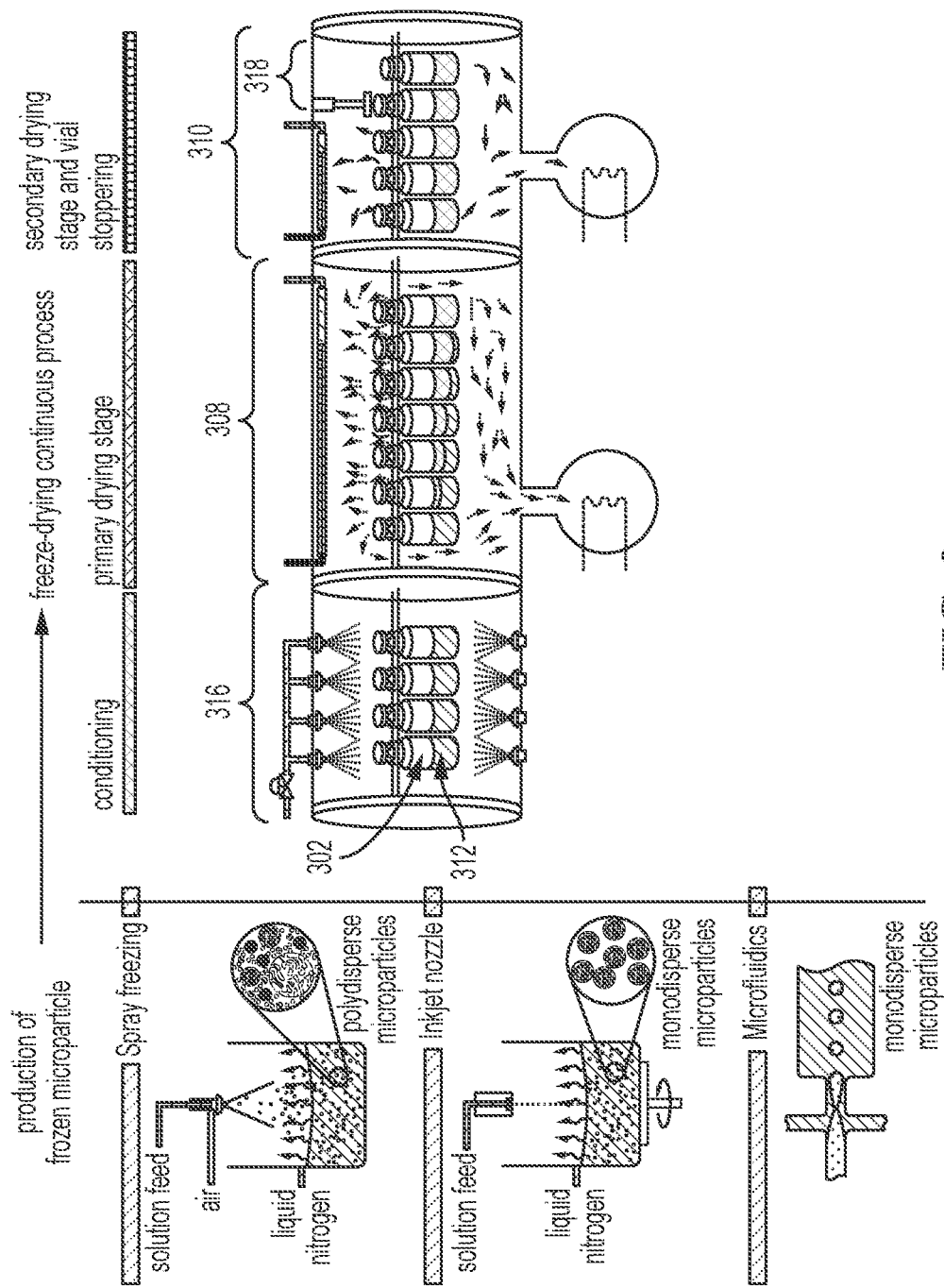
FIG. 3 provides a non-limiting schematic diagram of a continuous freeze-drying process for particle-based material and for spin-frozen products.

FIG. 3 shows a non-limiting illustrative schematic diagram of a continuous freeze-drying process in the case of particle-based material and spin-frozen products. The same concept can be applied for different vessels. The "production of frozen microparticle" (e.g., granules, spin-frozen materials) is outside of the scope of this disclosure. The process comprises the following steps:

a) a vessel (vial 302), already filled with a frozen composition 312 comprising a target product, is loaded into a conditioning module 316 until desired temperature is reached;

b) the vessel is moved into a primary drying module 308, where pressure and temperature are set to values in order to promote sublimation of ice from the frozen product;

c) the vessel is moved into a secondary drying module 310, where pressure and temperature are set to values in order to promote desorption of residual moisture from the dried product;

d) the vessel is moved into a pre-storage module 318, where a vial 302 is conditioned to storage temperature, backfilled with a proper inert gas and then closed.

Continuous Filling and Loading

The systems provided herein, in some embodiments, can process different types of products and can be used with different types of vessels. Certain embodiments provide a process for carrying out freeze-drying of (a) liquid solutions, (b) particle-based materials, (c) slurries, (d) pulps, (e) juices, (f) broths, (g) foams, and any other suitable starting composition. In some cases, the liquid material is an aqueous solution or suspension typical of the pharmaceutical industry. This disclosure can also be applied to solutions having solvents other than water. The starting composition may comprise antibiotics, vaccines, enzymes, drugs, serum and/or other chemical or biochemical components. The starting composition may comprise slurries, pulps, soups and/or juices typical of the food industry.

The starting composition can be processed using different vessels (e.g., vials of the desired dimension and material, syringes, double chamber cartridges, ampoule, phials, etc.).

In the case of liquid solutions, slurries, pulps and juices, in some embodiments the starting composition is continuously filled into vessels. In the case of particle-based material, in some embodiments the frozen particles are continuously filled into vessels. Once the vessel is filled, the vessel may be partially stoppered and then continuously loaded into the apparatus. In some embodiments, a fully automated system provides a sufficient number of vessels per minute to feed the freezing modules. Filling may be carried out in a sterilized and temperature-controlled environment.

Moving Vessels Through the Continuous Freeze-Drier

A number of non-limiting examples are provided for moving vials though the various modules, and facilitating the transfer of vials to/from environments working at different temperature and pressure.

Figure 4:
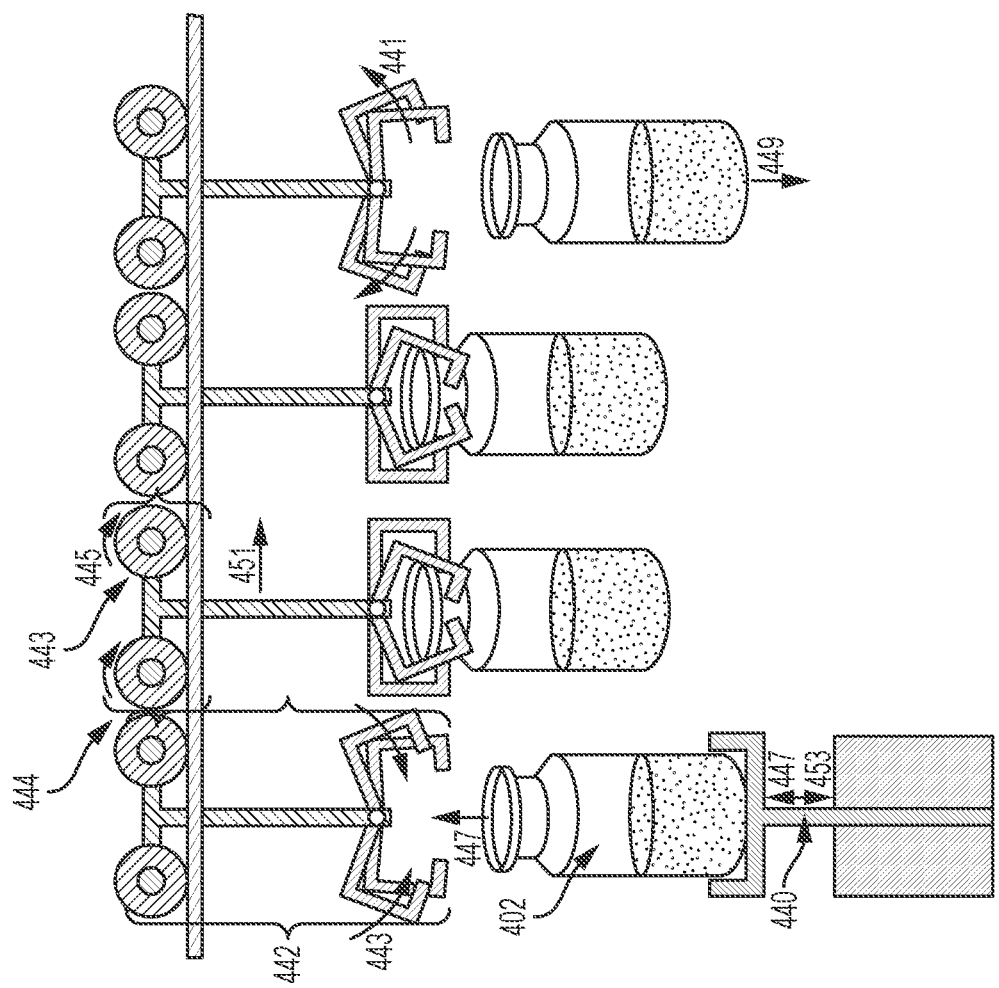
FIG. 4 shows a non-limiting side perspective view of an illustrative transport system based on the use of a gripper.

FIG. 4 shows a non-limiting first configuration for moving vials through a continuous freeze-dryer. As a vial 402 enters a new module, a piston 440 may lift vial 402 up in direction 447 so that the vial 402 is sufficiently close to a gripper 442. Then, the gripper 442 may grab the vial 402 (with gripper direction of motion 443) and hold onto the vial 402 (at which point the piston 440 retreats in direction 453) until the end of a module where the vial 302 is released (with gripper direction of motion 441) and travels in direction 449. The gripper 442 can effectively transport the vial 302 along the module through a trolley 444 that moves over a track in direction 451 (with wheels 443 turning in direction 445).

Figure 5:
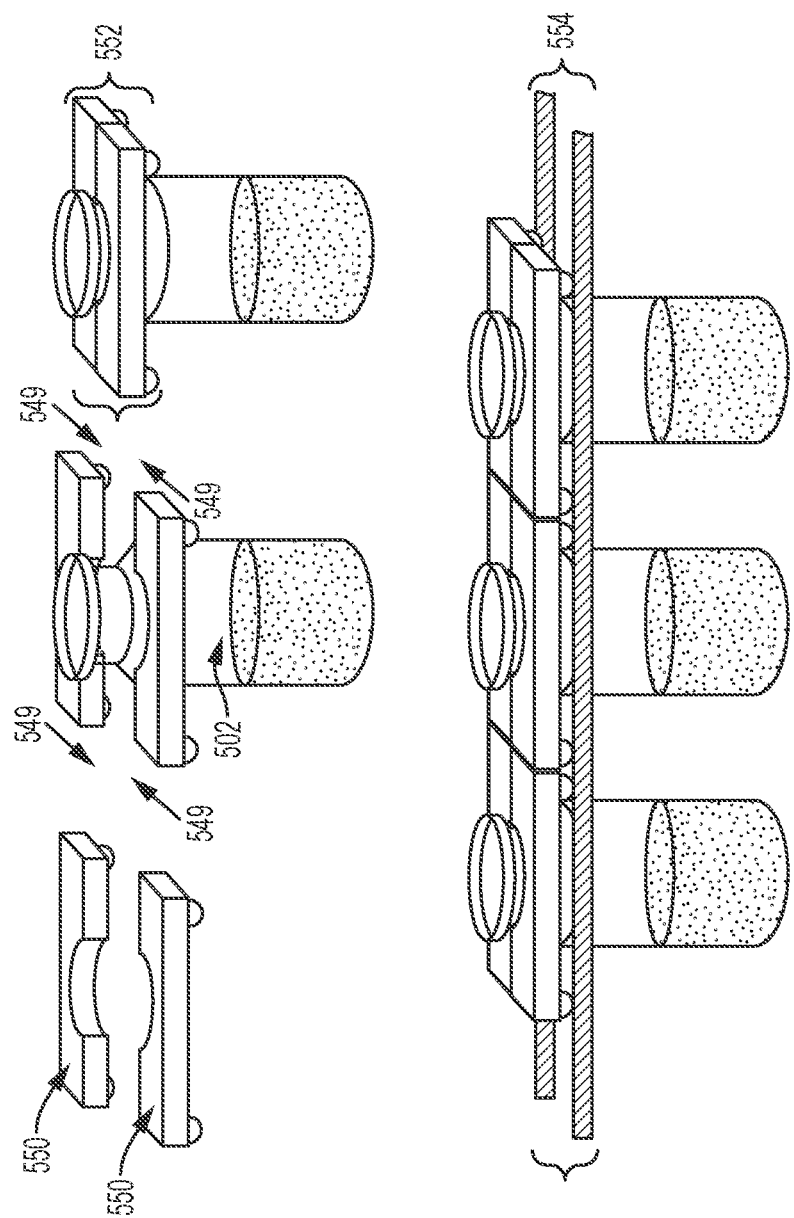
FIG. 5 shows a non-limiting side perspective view of an illustrative transport system based on the use of a conveyor.

FIG. 5 shows a non-limiting second configuration for transport of vials along a continuous freeze-dryer. As a vial 502 enters a new module, a piston (not shown) may lift vial 502 up so that the vial 502 is sufficiently close to two metallic semicircular parts 550. When the vial 502 reaches the correct position, the two metallic parts join one another along parallel directions 549, forming a skate 552, and may maintain that position until the end of the module where the vial is released, e.g., in a reverse manner as the metallic parts are separated from one another. The skate 552 can effectively transport the vial along the module sliding over a track 554.

Figure 6:
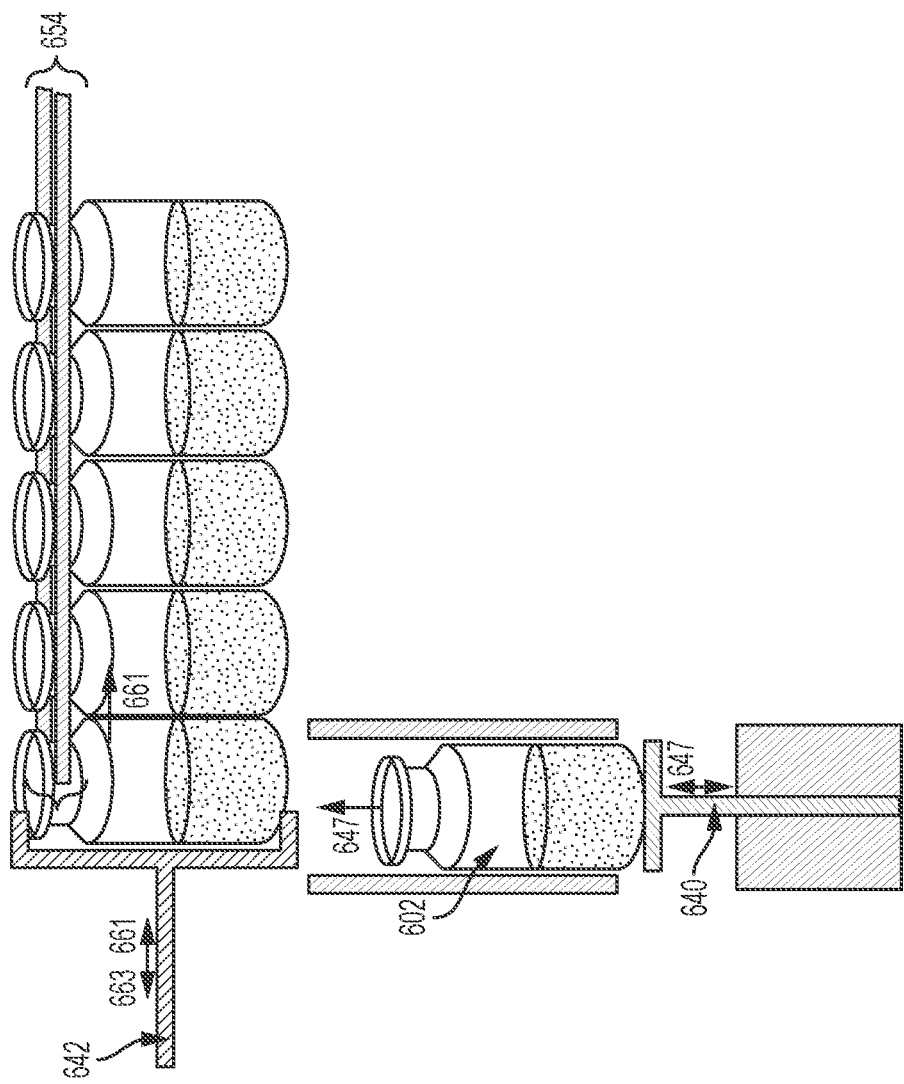
FIG. 6 shows a non-limiting side perspective view of an illustrative transport system where vials are moved along the equipment through a side-piston.

FIG. 6 shows another non-limiting system for moving vials along a continuous freeze-dryer. First, a vertical piston 640 lifts the vial 602 up in direction 647; then, a second piston 642 pushes the vial along a track 654 in direction 661 and, in this way, the entire row of vials is moved ahead in direction 661. The piston 642 is withdrawn in direction 663 between vials fed from piston 640.

Moving Vessels Between Modules

At least four different non-limiting configurations for load-lock systems to be used to transfer vessels between modules operating at different pressure and temperature are described herein.

Figure 7:
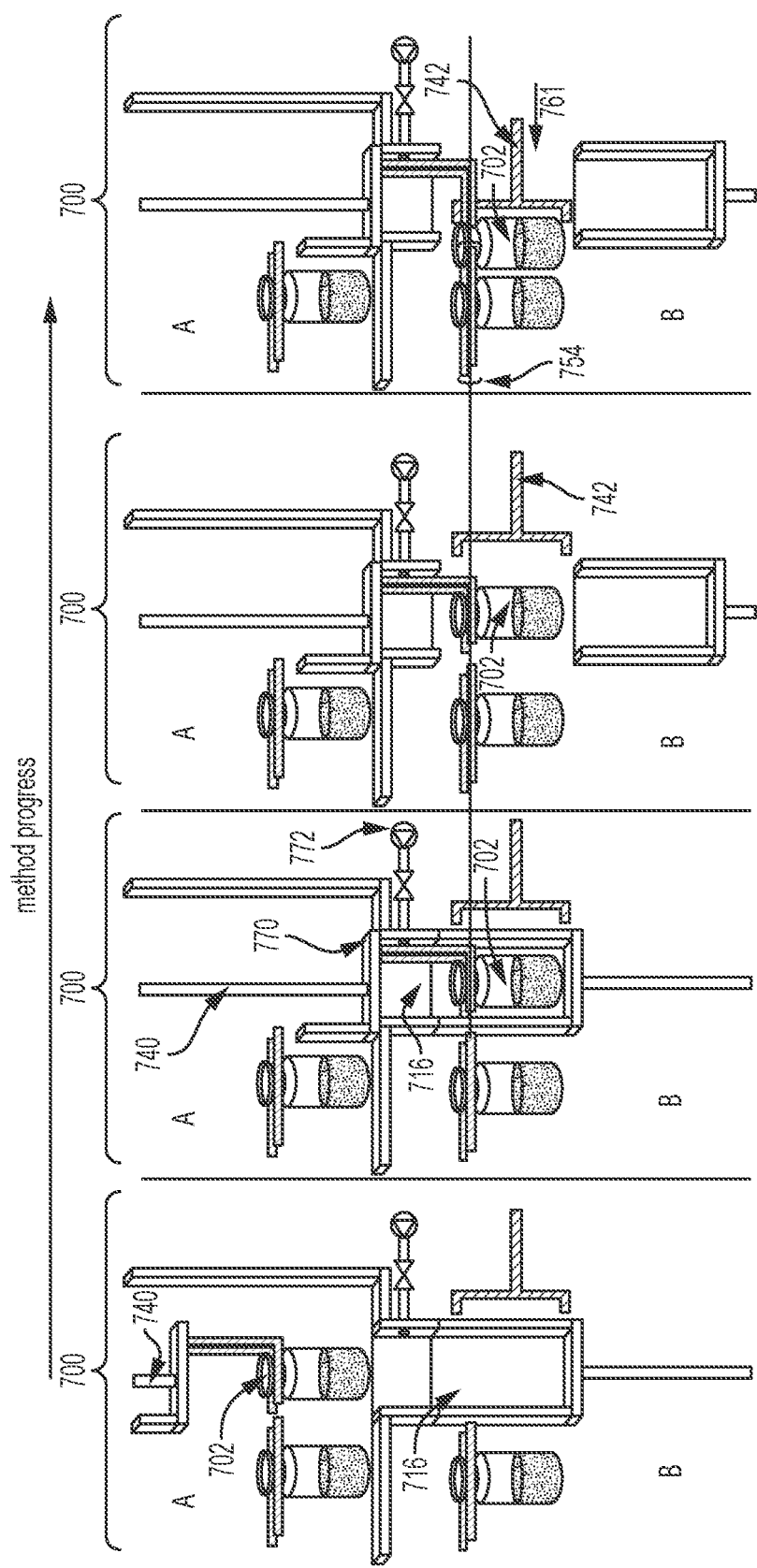
FIG. 7 is a non-limiting schematic of a load-lock system, based on the use of an elevator, that moves the vessels between two modules operating at different pressure and temperature from one another.

FIG. 7 shows a non-limiting example of a load-lock system 700 to be used to transfer the vessels from one module (e.g., module A) to a subsequent module (e.g., module B). At the end of each module, vessel 702 is picked up through a piston 740 and is transferred into an intermediate chamber 716, named a conditioning chamber 716. As vessel 702 is transferred into the conditioning chamber 716, a metallic sheet 770 at the base of the piston 740 isolates this chamber 716 from the module A (FIG. 7, second from left). After that, the pressure in chamber 716 is reduced through a vacuum pump, or increased by introducing a controlled flow rate of sterile gas at atmospheric pressure, by in-line pump 772. Once a desired pressure in chamber 716 has been reached, the conditioning chamber 716 is opened (FIG. 7, second from right) and a second piston 742 pushes the vessel 702 along direction 761 through the track 754 of module B (FIG. 7, right). Once the vessel 702 has been transferred, the conditioning chamber 716 is closed, the pressure is adjusted according to that of module A (using in-line pump 772), and finally conditioning chamber 716 is re-opened using piston 740. This apparatus can also be used to induce nucleation by vacuum-induced surface freezing; see FIG. 2.

Figure 8:
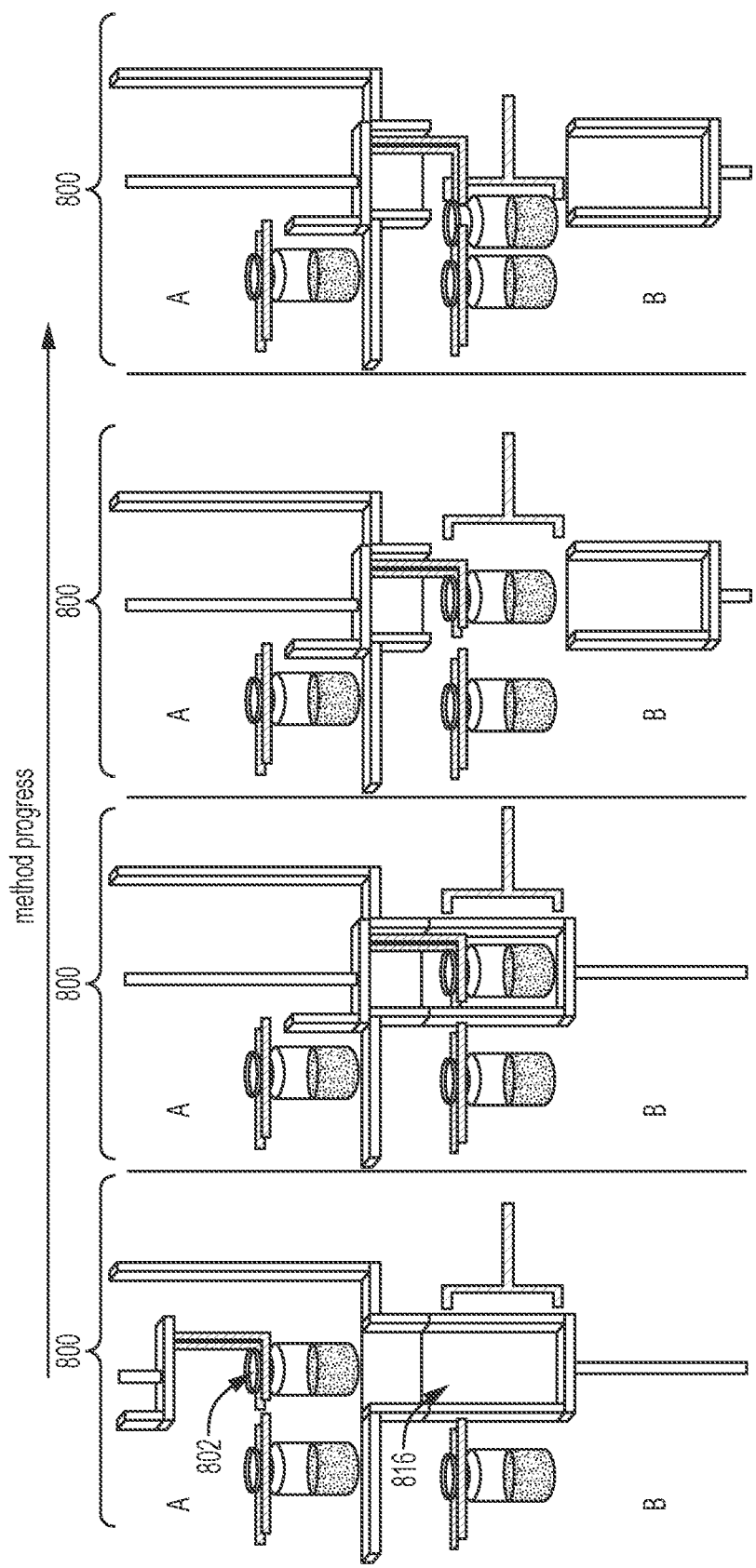
FIG. 8 is a non-limiting schematic of a load-lock system, based on the use of an elevator, that moves the vessels between two modules operating at different pressure and temperature from one another, wherein the pressure inside the conditioning chamber is not controlled.

FIG. 8 is a non-limiting alternative apparatus 800 (and associated methods) to the load-lock system 700 shown in FIG. 7. In this version, once the vessel 802 has been transferred into the conditioning chamber 816 and isolated from module A, the conditioning chamber 816 is re-opened without any preventive pressure regulation. As the volume of the conditioning chamber is much smaller than that of module B, the pressure disturbance introduced by this operation is negligible.

Figure 9:
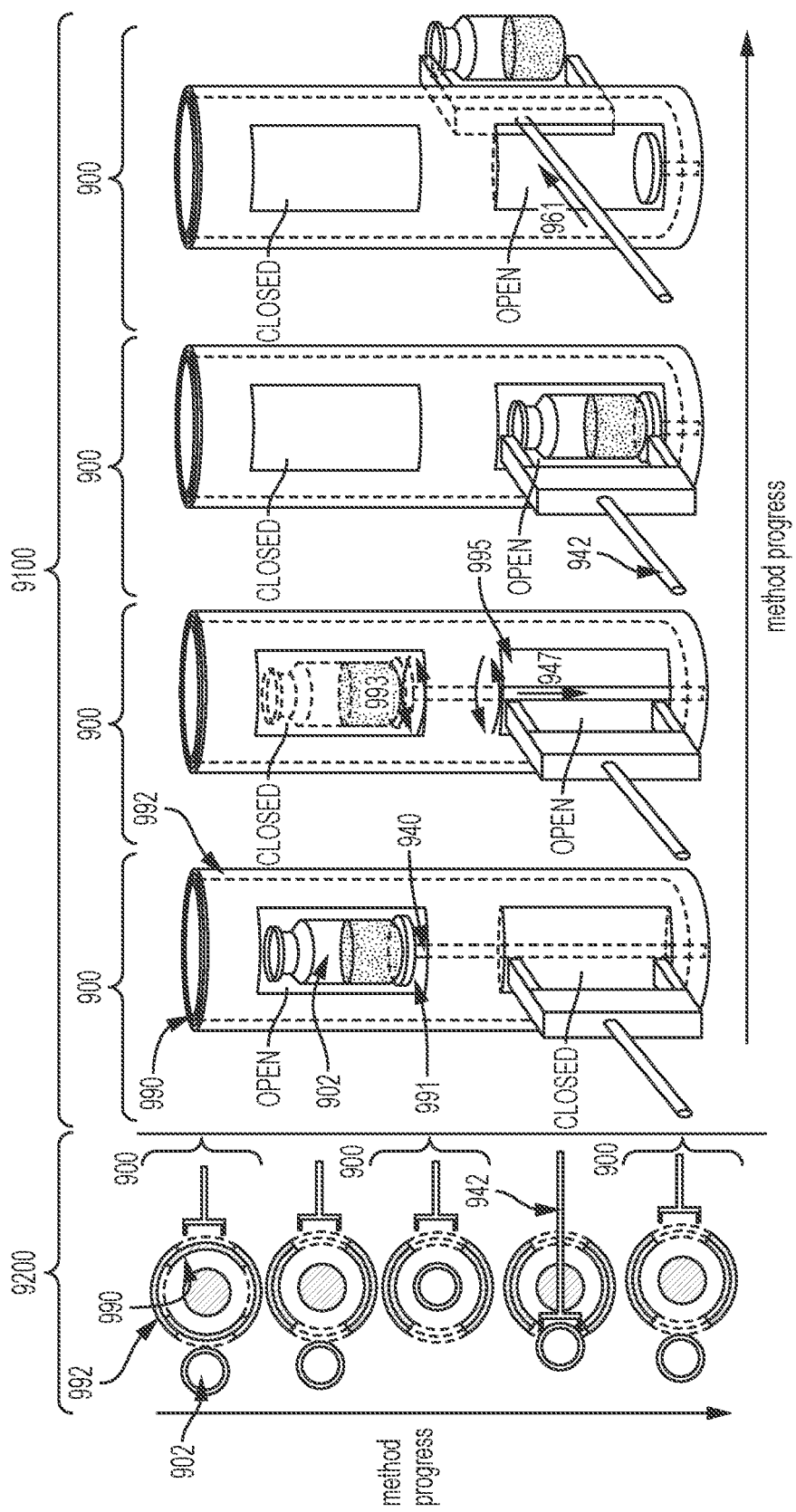
FIG. 9 shows non-limiting top and side perspectives of a load-lock system that involves the use of an elevator and a rotating device.

FIG. 9 shows a non-limiting schematic diagram in perspective view 9100 and bird's eye view 9200 of an alternative load-lock system 900 (also referred to herein as a load-lock apparatus) to transfer vessel 902 between two modules (e.g., module A and module B). The apparatus comprises two coaxial cylinders: an internal cylinder 990 that can rotate, and an external cylinder 992 that remains fixed. As can be seen in FIG. 9, the vessel 902 enters the load-lock system from a first module (9200, second-fromtop to third-from-top), through upper opening 991; then, the internal cylinder 990 of the apparatus rotates 90 degrees as illustrated by rotation direction 993 and piston 940 moves vial 902 in direction 947. During rotation, upper opening 991 is closed and then a new opening 995 appears in the lower part. At this point, a piston 942 pushes vessel 902 in direction 961 out of the load-lock system over a track (not shown) of a second module.

Figure 10:
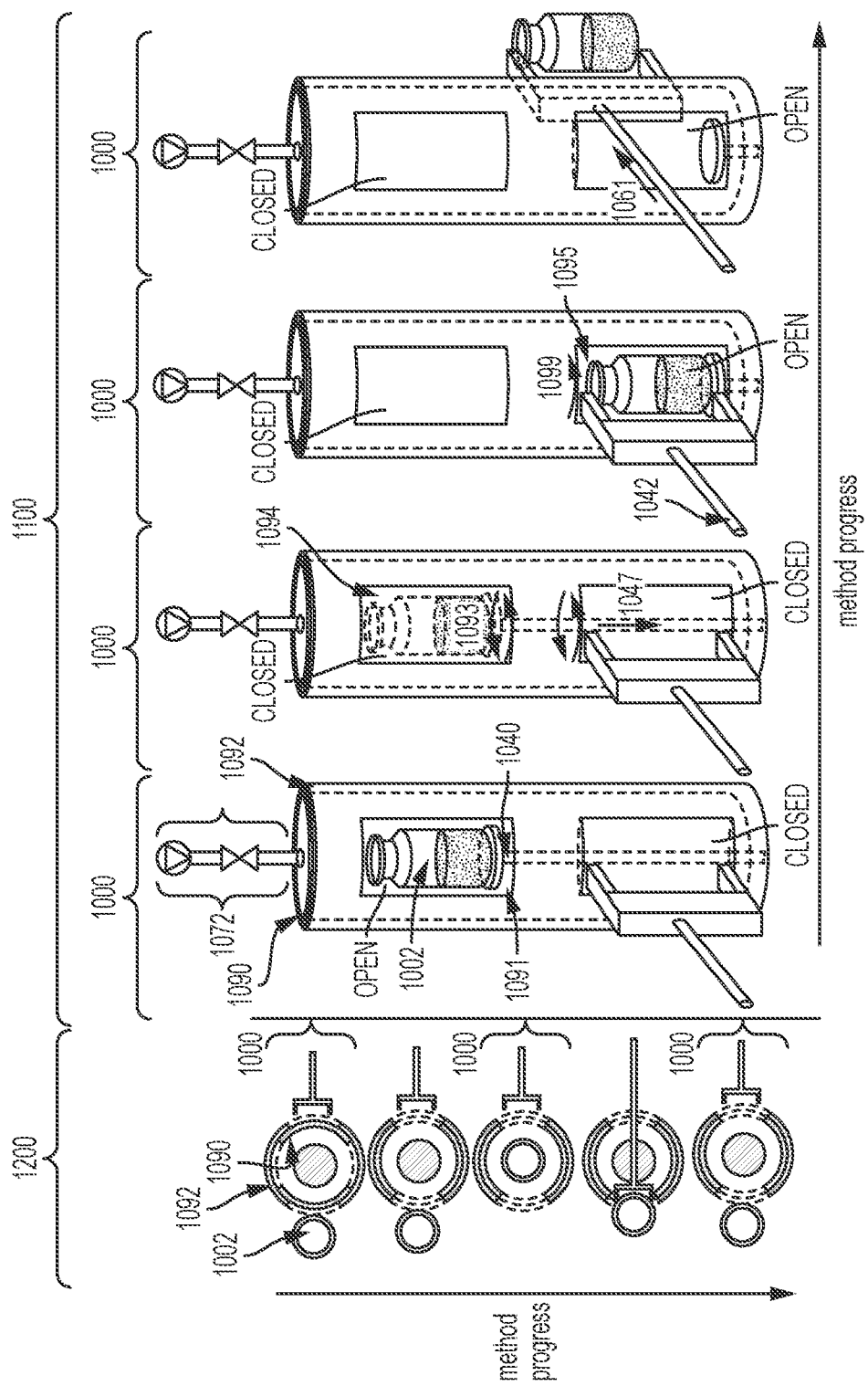
FIG. 10 shows non-limiting top and side perspectives of a load-lock system that involves the use of an elevator and a rotating device and pressure control.

FIG. 10 shows a non-limiting alternative load-lock system 1000 (and associated methods) to the load-lock system 900 described in FIG. 9, in perspective view 1100 and bird's eye view 1200. The apparatus comprises two coaxial cylinders: an internal cylinder 1090 that can rotate, and an external cylinder 1092 that remains fixed. Vessel 1002 enters the load-lock system from a first module (1200, second-from-top to third-from-top), through upper opening 1091; then, internal cylinder 1090 of the load-lock system 1000 rotates 90 degrees in direction 1093, closing upper opening 1091 and isolating load-lock chamber 1094. Vessel 1002 is lowered down through piston 1040 in direction 1047 and the pressure surrounding vessel 1002 is regulated through a vacuum system 1072. After that, the inner cylinder 1090 rotates 90 degrees in direction 1099 creating an opening 1095 in the lower part of the apparatus through which the vessel exits the load-lock apparatus in direction 1061, via a side-piston 1042, and moves over a track of a second module (not shown).

Figure 11:
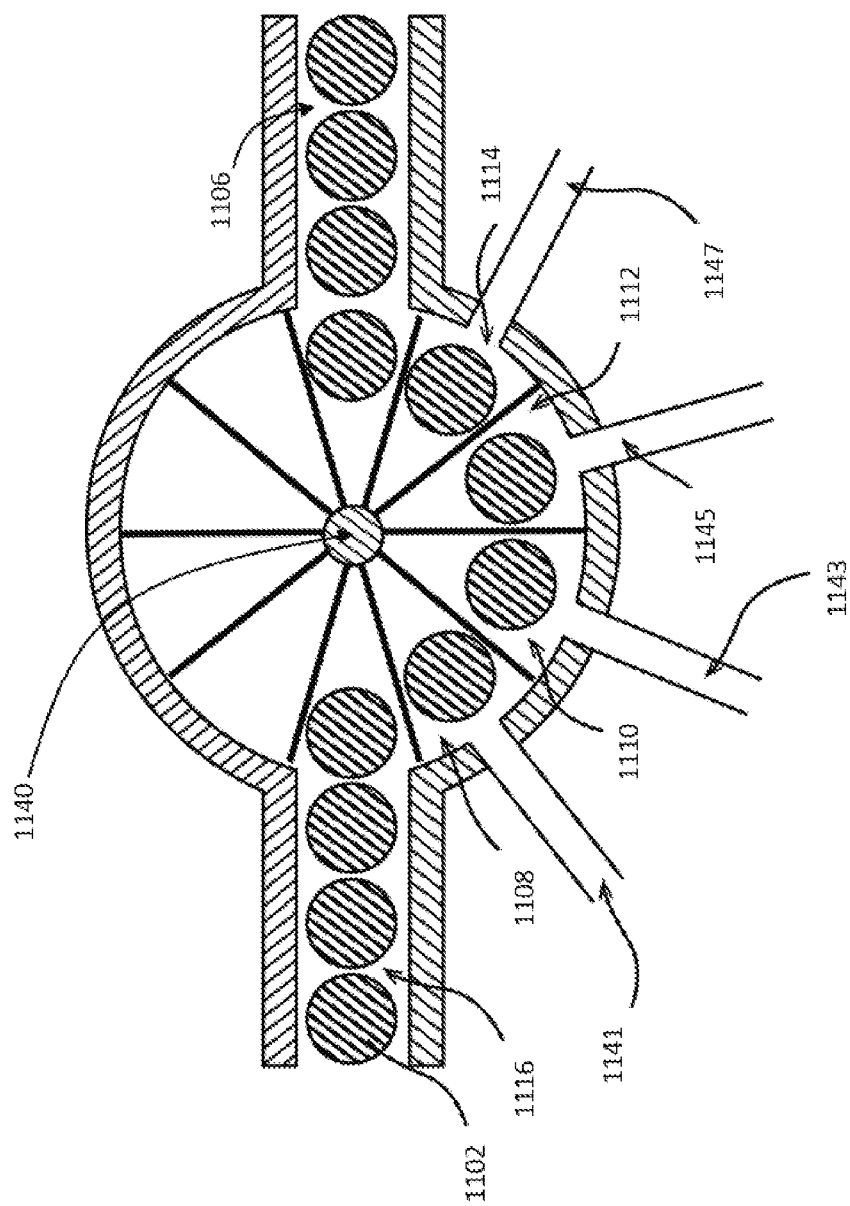
FIG. 11 shows a non-limiting top perspective of a rotating load-lock system.

FIG. 11 shows a non-limiting schematic diagram of a rotating load-lock system. As vessel 1102 enters the load-lock apparatus, a rotary valve 1140 moves the vessel ahead. During this transition, the valve 1140 can undergo different values of pressure, decreasing or increasing pressure, depending on the request. This rotating load-lock system can also be used to induce solvent nucleation by vacuum-induced surface freezing. Nucleation may here be promoted by vacuum. As vial 1102 is picked up, vial 1102 travels through three subsequent chambers, 1108, 1110, and 1112 and is exposed to progressively decreasing pressure. Vacuum promotes solvent evaporation on the top surface of a liquid composition in vial 1102 and hence its cooling. This phenomenon may stabilize solvent clusters and allow formation of stable nuclei and, thus, induce nucleation at a desired temperature, e.g., a temperature of the product at the end of the conditioning chamber. In chamber 1114, atmospheric pressure is re-established. In principle, vacuum induced nucleation can be achieved by using only two chambers, chamber 1108 for vacuum and chamber 1114 for re-stablishing atmospheric pressure. More specifically, e.g., vessel 1102, coming from conditioning chamber 1116 which is at atmospheric pressure, moves into rotary valve 1140, where pressure is decreased to the desired pressure. During its passage into the valve 1140, vessel 1102 may experience decreasing pressure (at 1108, 1110, 1112) which may assure that nucleation occurs instantaneously. The valve 1140 is connected to a vacuum system and a controlled leakage line to regulate the final pressure (at connections 1141, 1143, 1145, 1147). After chamber 1112, vessel 1102 exits rotary valve 1140 and is pushed, over a track (not shown), into the next module 1106 (e.g., a freezing module).

The Freezing Module

As can be seen in FIG. 1, FIG. 2, and FIG. 3, a vessel may be filled in with a given volume of liquid or frozen particles and then transferred through a load-lock system into a freezing module. Here, vessels may be suspended and moved over a moving track using one the various strategies depicted in FIG. 4, FIG. 5, and FIG. 6.

As can be seen in FIG. 12, a non-limiting system for the continuous freeze-drying of a composition is provided. A system provided in FIG. 12 comprises a first module (e.g., freezing module 1206) and a second module (e.g., primary drying module 1208) and an interface apparatus (e.g., load-lock system 1230) connecting the first module to the second module. A first module 1206 in FIG. 12 comprises a freezing chamber and a second module 1208 in FIG. 12 comprises a drying chamber. In FIG. 12, vessels 1202 comprising a composition 1212 are suspended in a line along a conveyor 1214.

A freezing module in FIG. 12 comprises three sub-modules in some embodiments: (A) a conditioning module 1216, (B) a load-lock system 1231 where controlled nucleation can eventually occur, and (C) an equilibration/freezing module 1206. In a conditioning module 1216 in FIG. 12, in some embodiments, a vessel 1202 containing a composition 1212 (vessel 1202 having been filled at filling module 1204) is cooled down and equilibrated to a desired temperature by adjusting temperature and flow rate of a cryogenic gas using cooling system 1224. At the end of conditioning module 1216, vessel 1202 may enter load-lock system 1231. After entering, vessel 1202 can simply be transferred to the subsequent module (freezing module 1206), or vessel 1202 is exposed to a vacuum that makes nucleation occur and vessel 1202 then is transferred to the subsequent module. This last operation can be effectively done if for example the starting material is liquid. Once vessel 1202 has been transferred to freezing module 1206, its temperature is lowered until completion of solution solidification.

Table 1 shows an overview of operations that may be involved in freezing modules depending on the initial state of a material to be freeze-dried.

TABLE 1

Freezing operations for different types of material

| | | Continuous freezing | | |
|---|---|---|---|---|
| Materials | Filling | Conditioning module | Nucleation chamber | Freezing module |
| Liquid solutions, slurries, broth, pulps, juices and foam | Yes | Yes (not compulsory) | Yes (not compulsory) | Yes |
| Particle-based materials | Yes | Yes (not compulsory) | No | No |

Figure 30:
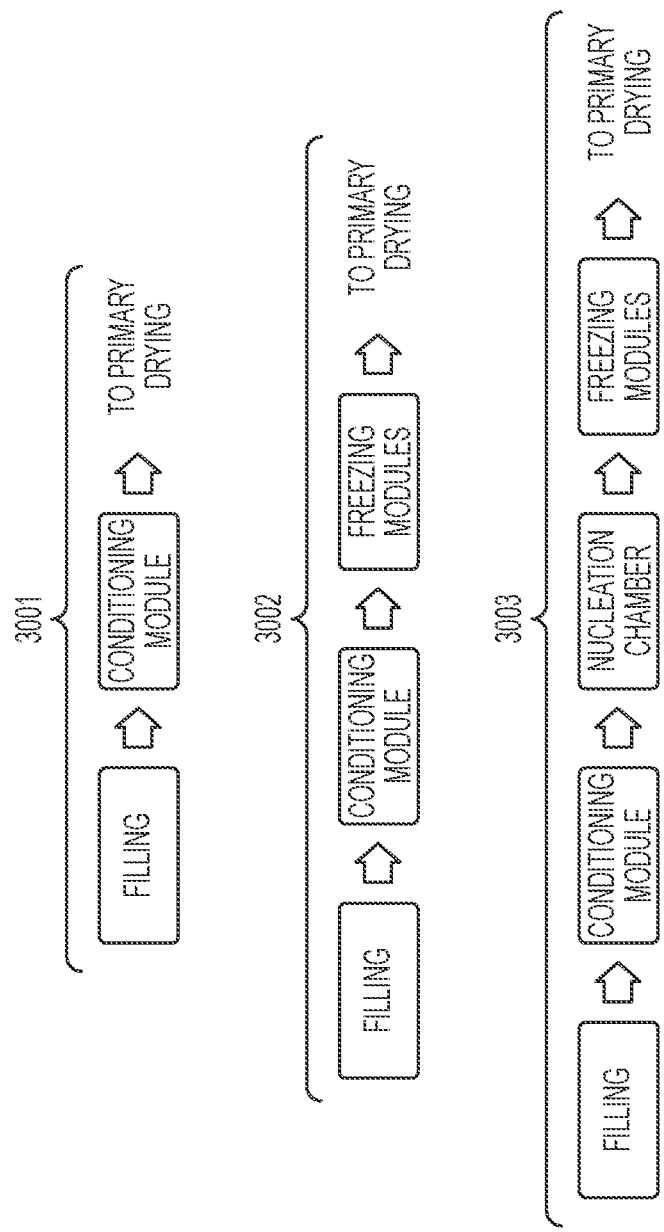
FIG. 30 provides a non-limiting schematic diagram of operations that a continuous lyophilizer may carry out for different states of a product to be freeze dried.

FIG. 30 depicts a summary of operations that a continuous lyophilizer may carry out depending on the physical state of the product to be freeze-dried: 3001, no nucleation (e.g., particle-based materials; 3002, spontaneous nucleation (e.g., liquid solutions, slurries, broth, pulps, juices, foam, etc.); and 3003, controlled nucleation (e.g., liquid solutions, slurries, broth, pulps, juices, foam, etc.).

The Conditioning Module

In the conditioning module, in some embodiments, vessels are conditioned to a desired temperature by flowing a cryogenic fluid (e.g., nitrogen gas, liquid nitrogen) at a controlled temperature and flow rate. In some embodiments, vessels are suspended over a moving track and moved along a module using an apparatus comprising a track described herein. In some embodiments, vessels move along a conditioning module with a velocity that is determined by a drying module. In such embodiments, temperature and flow rate of a cryogenic fluid may be adjusted so that the vessels reach their desired temperature before leaving the conditioning module.

In some embodiments, conditioning of a starting composition to be freeze-dried improves the homogeneity of the composition during freezing by resulting in all vessels having the same temperature as one another as they exit from a conditioning module.

Control of Nucleation Temperature

In accordance with some embodiments, nucleation temperature, for a composition to be processed by a system and method described herein, is controlled in order to make both the drying behavior and the product morphology more uniform. Non-limiting examples of methods to control nucleation temperature include ultrasound, ice fog, and pressure disturbance. All of these methods can be integrated into a nucleation module, but mainly vacuum-induced surface freezing is discussed herein, which uses a vacuum system to instantaneously induce a nucleation event in a composition herein, at least because in some embodiments, a vacuum system can easily be added to a load-lock system used to load vessels into the freezing module. Nucleation in a composition may be induced by reducing pressure directly inside a load-lock chamber; the pressure reduction may promote partial evaporation of a solvent in the composition and hence cool the solution, facilitating formation of stable nuclei. In some embodiments, this method results in consistent nucleation temperature across multiple vessels and therefore results in consistent ice morphology among the vessels.

The Freezing Module

In some embodiments, in a freezing module, vessels are cooled down by natural convection or forced air circulation until complete solidification of the product occurs. A vessel in some cases is suspended over a moving track and is introduced into a freezing module.

In a freezing module, heat may be prevalently transferred by gas convection and radiation from the surroundings. In order to speed up the freezing process and make heat transfer between the freezing module equipment and a vessel more uniform, a cryogenic fluid can be forced to move along the freezing module, similarly to the conditioning module. In such cases, external surfaces of the vessel may be equally flushed by the cryogenic fluid (e.g., cryogenic gas), resulting in significantly reduced heterogeneity of heat flux relative to that in conventional batch freezing.

Different freezing protocols, including annealing that makes the frozen product morphology further uniform, can be performed by modulating the velocity of cryogenic fluid and its temperature. Additionally, these two process parameters can be adjusted to control the duration of the freezing and, thus, replicate the forward velocity of the vessels selected for the drying module on the freezing module.

The Primary and Secondary Drying Module

In some embodiments, each drying module (e.g., primary drying module 1208 and secondary drying module 1210 in FIG. 12) is connected to a vacuum system (e.g., centralized vacuum system 1222 in FIG. 12), condenser and vacuum pump, which allows control to the desired pressure, while temperature of the equipment surfaces is controlled by adjusting the temperature of the heat transfer fluid, silicone oil, by a refrigeration (cooling) system (e.g., 1224 in FIG. 12) as shown in FIG. 12. An external heat exchanger may be used to control the temperature of a heat transfer fluid, silicone oil, which is flowing within the equipment walls. In some embodiments, a chiller may be used, and then an electrical resistance may be used to adjust to a final temperature. As an alternative, an infrared source of heating the product may be used during drying.

In this configuration, in some embodiments, the vessels are not in contact with the shelves, and heat is primarily transferred by radiation. In fact, low pressure, below 1 mbar, may make heat transfer by convection and conduction negligible with respect to the radiative contribution. This configuration may allow the heat to be uniformly transferred to the vessel, avoiding those issues that are typical of batch freeze-drying. Besides that, temperature and pressure gradients within the equipment may no longer represent a cause of heterogeneity in heat transfer because vessels, following the same path, experience the same identical conditions.

In this module, heat may be supplied by radiation through temperature controlled surfaces, but can potentially be transferred by using other technologies such as infrared radiation or microwave. In some embodiments, as heat is primarily transferred by radiation, the control of the temperature of the product being dried may be much easier and allows uniformity in heat transfer and, thus, in drying behavior.

The same equipment configuration may be suitable for both the primary drying module and the secondary drying module; the two modules may in some embodiments be identical but operate at different pressures and temperatures from one another.

The continuous equipment can be adapted to carry out atmospheric freeze-drying. In such cases, the primary and secondary drying modules may operate at atmospheric pressure; sublimation and desorption are promoted by exposing the product to a controlled flow of dried nitrogen, or another gas, at controlled temperature. In this last case, in some embodiments, the gas at the outlet of the drying chamber is treated in a system that removes its moisture, its temperature is adjusted through an appropriate cooling system, and finally is re-circulated in the drying chamber.

Backfill and Stoppering/Closing

In some embodiments, the system may comprise a module for backfilling and stoppering/closing of the vessel. In some embodiments, at the end of the secondary drying module, a piston pushes down and the stopper is placed over the vessel, sealing the vessel under vacuum conditions. In some embodiments, this procedure avoids any contamination of the product.

Design of the Modules

Figure 13:
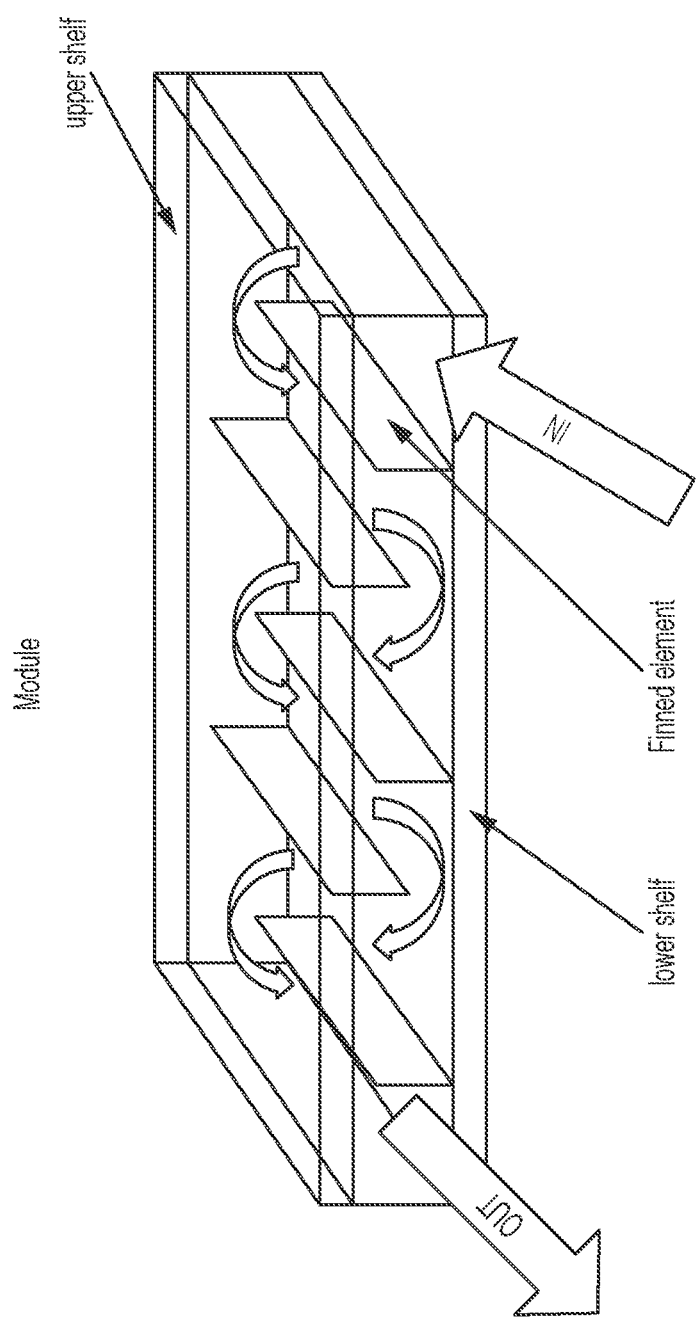
FIG. 13 is a non-limiting schematic of a freezing/drying module wherein the vessels are moved along the equipment following an illustrative non-linear path.
Figure 14:
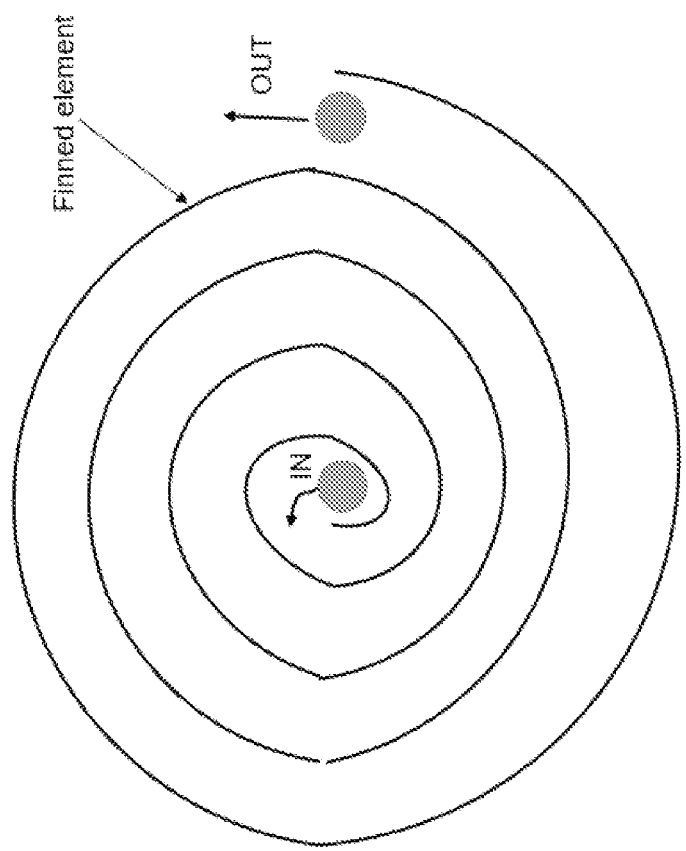
FIG. 14 is a non-limiting schematic of a freezing/drying module wherein the vessels are moved along the equipment following a spiral path.

In order to minimize the amount of space occupied by the equipment, in some embodiments, the vessels can flow within the various modules, both freezing modules and drying modules, as either a straight path, e.g. along modules 1216, 1206, 1208, 1210 in FIG. 12, or more compact paths, e.g., as depicted by directional arrows in FIG. 13 and FIG. 14.

The following examples are intended to illustrate certain embodiments of the present disclosure, but do not exemplify the full scope of the disclosure.

EXAMPLES

In this section, non-limiting examples of results that can be obtained by presently disclosed systems (e.g., continuous lyophilizers) and methods are shown.

Example 1—Freezing

Freezing conditions may in some embodiments influence the size and the shape of frozen crystals (e.g., ice crystals) in a composition, determine the microstructure of the product (e.g., of freeze-drying), and finally, affect the intra- and inter-vessel heterogeneity within a production. Freezing may impact not only product quality but also the rate of sublimation and desorption during primary and secondary drying.

Relative aspects of a reference batch process, in which vessels were loaded onto temperature-controlled shelves (and other conventional batch techniques were employed), were compared with those of a continuous-convective process using, as a model composition, aqueous solutions of excipients mannitol 5% w/w, sucrose 5% w/w, and lactose 5% w/w. In these tests, glass vials were used as vessels which were filled with 3 ml of solution. For continuous freezing, vials were lined up over a track.

Figures 15A, 15B:
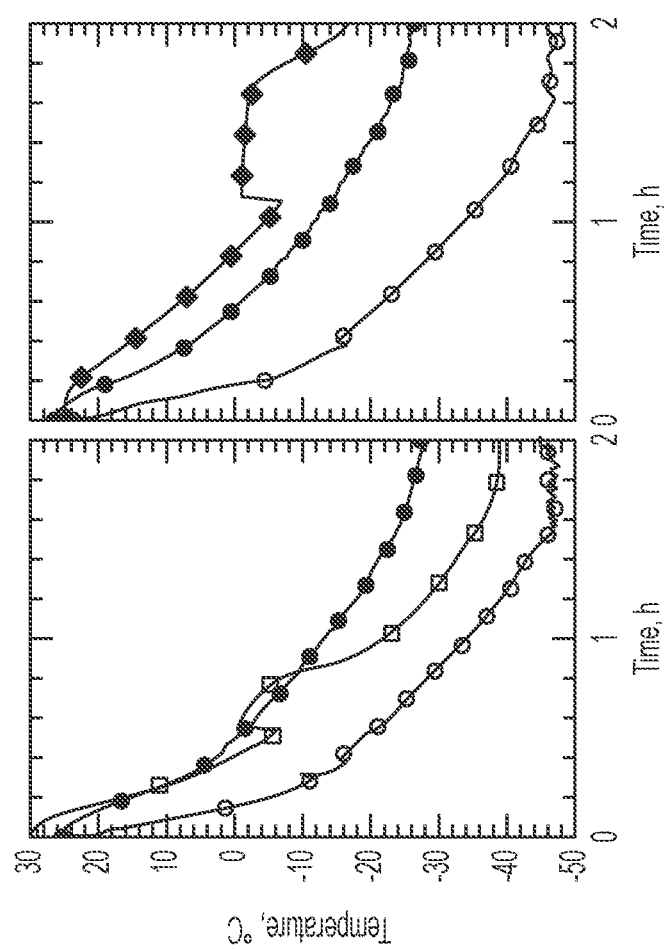
FIG. 15A and FIG. 15B depict non-limiting temperature profiles during freezing in the case of conventional batch freezing (FIG. 15A) and continuous freezing (FIG. 15B), wherein temperature of the (○) shelf/equipment surface and of the (●) gas within the drying chamber are also shown.

FIG. 15A and FIG. 15B show examples of the results obtained. In particular, temperature trends are shown for the composition being dried, mannitol 5% w/w, for the shelves in the case of batch freezing (e.g., FIG. 15A), and for the equipment surfaces and the cryogenic gas for the continuous freezing (e.g., FIG. 15B).

Where batch freezing is used, (e.g., FIG. 15A), it was observed that the mean temperature of the composition was, as expected, between the shelf temperature and the temperature of air within the chamber. It was also observed that temperature gradients within the frozen composition were significant, between about 1 degrees Celsius and about 5 degrees Celsius depending on the filling volume, with the lowest temperature corresponding to the vial bottom and the highest temperature corresponding to the top surface of the composition. Once nucleation occurred, it was also observed that crystal growth was much faster close to the bottom of the vial with respect to the top surface of the liquid being frozen. Because of that, the ice morphology changed along the axial position of the composition.

In the case of continuous freezing, the liquid sample was prevalently cooled down by convection of a cryogenic gas, consisting of nitrogen, trapped within the freezing chamber. FIG. 15B shows the temperature evolution of a sample in a vial. In this case, all of the surfaces of the vial experienced identical conditions, because the vessels were immersed within the cryogenic gas, having uniform temperatures nearby the vial, and no contact with the shelf occurred. No preferential direction of heat removal occurred and the solution (composition) had a similar thermal history throughout the whole volume. It can thus be hypothesized that, after nucleation, crystal growth uniformly occurred within the filling volume (that is, within the volume of the composition), leading to a much more uniform product structure as discussed herein.

In the case of continuous freezing, temperature and flow rate of a cryogenic fluid can be adjusted so as to perform different freezing conditions on a composition and, hence, manipulate the porous structure of the lyophilized product resulting from processing the composition using a system and method described herein. In some embodiments, if air is used as cooling medium and its forward velocity can be modulated in the range of between 0 m s$^{-1}$ and 10 m s$^{-1}$, the heat transfer coefficient can be modified in the range of between 5 W m$^2$ K$^{-1}$ and 80 W m$^2$ K$^{-1}$. Overall, it was observed that these conditions allowed the modification of pore sizes in the range from 20 microns to 100 microns at constant nucleation temperature, for example approximately negative 8 degrees Celsius.

Figure 16:
FIG. 16 shows a non-limiting comparison of a lyophilized product as produced using both conventional freeze-drying (left) and continuous freeze-drying (right)
Figure 31:
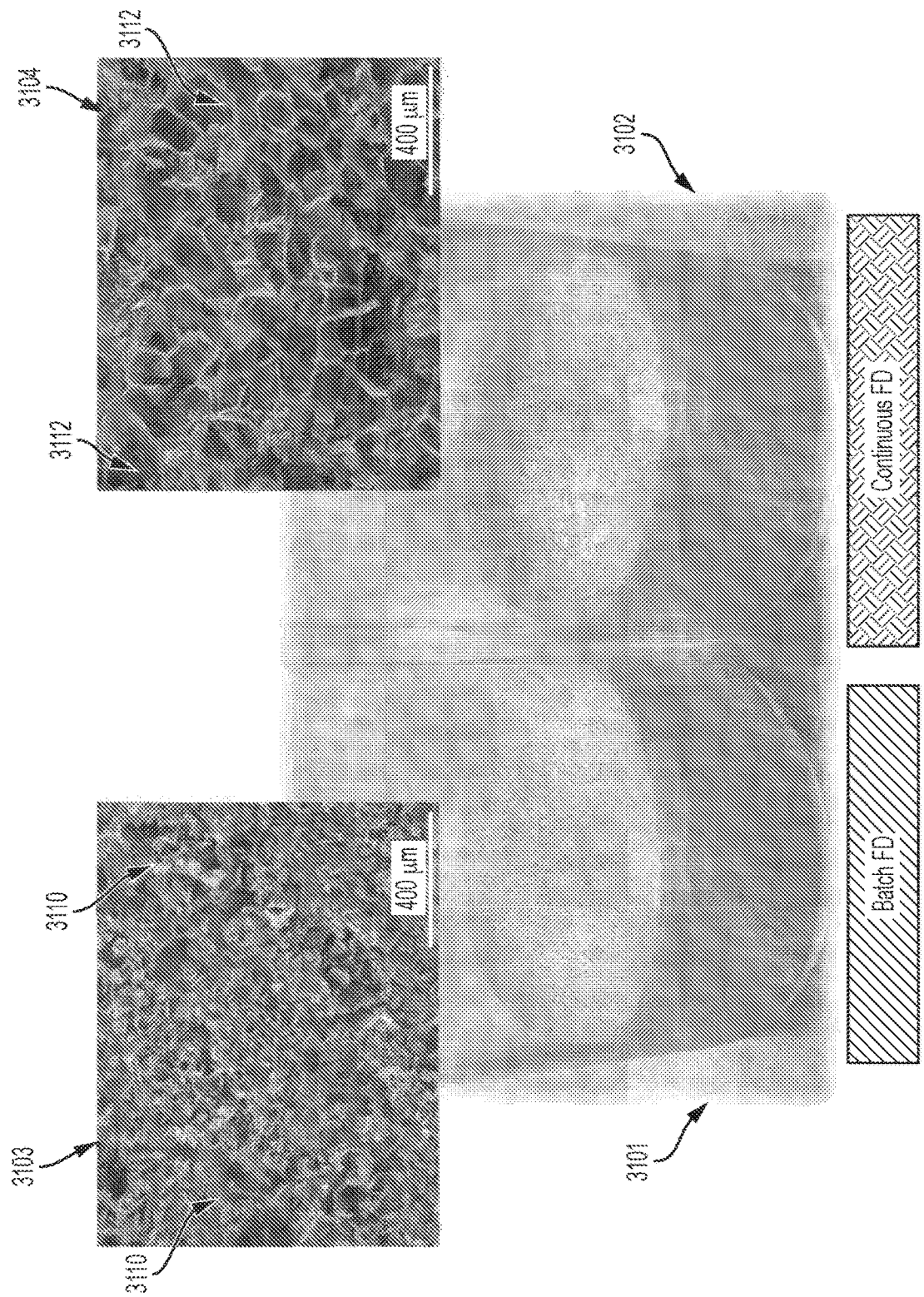
FIG. 31 shows non-limiting photographs and scanning electron micrographs of a product of batch freeze-drying (FD) and a product of continuous freeze-drying.

In conclusion, the lyophilized product as obtained by a non-limiting continuous lyophilizer met the aesthetic requirements of the pharmaceutical industry. FIG. 16 shows two lyophilized samples, containing mannitol, as obtained by the batch lyophilizer (left, lyophilized sample 1604 in vial 1601) and continuous lyophilizer (right, lyophilized sample 1606 in vial 1602). Corresponding scanning electron micrographs are shown in FIG. 31. FIG. 31 shows photographs and scanning electron micrographs, each scanning electron micrograph with a scale bar of 400 microns, of a product of batch freeze-drying (FD) (left, photograph 3101 and scanning electron micrograph 3103) and continuous freeze-drying respectively (right, photograph 3102 and scanning electron micrograph 3104), each product containing mannitol, according to some illustrative embodiments. An increased average pore size may result from continuous freeze-drying by a method described herein relative to batch freeze-drying a similar sample (see, e.g., pores 3110 from batch freeze-drying and pores 3112 from continuous freeze-drying). In some embodiments, continuous freeze-drying resulted in up to 5 times shorter of a cycle time compared with batch freeze-drying. The non-limiting continuous freeze-drying configuration and method may have contributed to large pores, with constant shelf temperature during freezing. The larger pores may have corresponded to smaller resistance to vapor flow and therefore shorter drying time. Breaks during a typical batch production may be between or equal to 20% and 50% of the total cycle time. By reducing the total cycle time using continuous freeze-drying methods as described herein, energy consumption may be reduced as well.

Example 2—Drying

Uniformity in Drying Behavior

In batch freeze-drying, heat transfer significantly varied with the position of the vessel within the batch. A batch of vessels was conventionally divided into zones, as shown in FIG. 17A. The vessels at the edge of the batch received more heat compared to those located in the center, due to the contribution of radiation from chamber walls. This heterogeneity is well described in FIG. 17B, which shows a spatial distribution of heat flux during primary drying, as calculated by a standard gravimetric procedure. FIG. 17C also shows that the maximum product temperature reached during primary drying was related to the position of vials. For example, the vessels at the edge of the batch had a product temperature that was 5 degrees Celsius higher than that of the vessels loaded in the center of the batch. This is typical behavior in batch freeze-drying, which leads not only to tremendous differences in terms of drying times among the vessels of the same batch, but also to issues during the scale-up of the process from the laboratory to production scale, or more generally the lack of control of the drying process. Moreover, the process is usually designed based upon the maximum temperature allowed to be reached by the product during primary drying; since this temperature changed with the position of the vessel within the drying chamber, it would be a risk to design a cycle that is efficient for edge-vessels, but too precautionary for vessels placed in the center, making the process not efficient and longer than that would be necessary if heat were uniformly distributed over a batch of vessels.

By contrast, when a continuous lyophilizer disclosed herein was used, all the vessels underwent virtually identical heat transfer conditions; see, e.g., FIG. 17D. In FIG. 17E and FIG. 17F, heat flux and maximum product temperature is shown for a continuous lyophilizer in the case of different clearances, that is the distance between a vessel surface and that of the equipment (e.g., chamber walls, floor, or ceiling). Both heat flux and product temperature did not change with the position of the vessel on the track.

Figure 18:
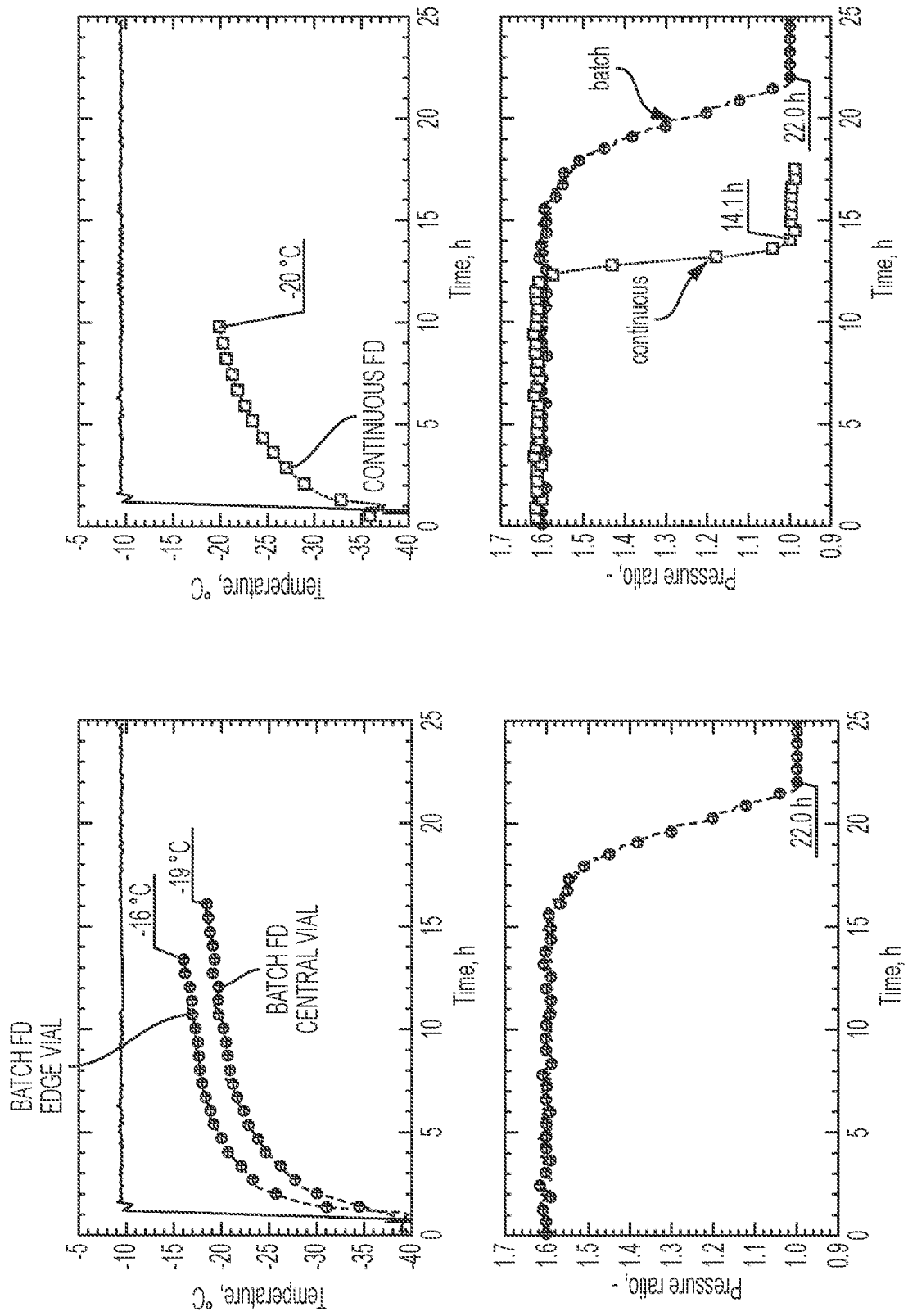
FIG. 18 shows non-limiting illustrative plots comparing heat flux in batch freeze-drying (left) and in continuous freeze-drying (right)

FIG. 18 compares drying behavior, product temperature, and drying time as observed for a batch lyophilizer and a continuous lyophilizer. This comparison was done at constant temperature of a heat transfer fluid and pressure. The continuous lyophilizer showed the shortest drying time, 14 hours (vs. 22 hours for batch), and the lowest product temperature, negative 20 degrees Celsius (vs. negative 16 degrees Celsius for batch). Drying time was estimated by comparing a pressure signal given by a thermo-conductive gauge and a capacitive one (e.g., by a pressure ratio in FIG. 18), which is a well-established method in the literature. The onset time and offset time of this pressure signal was also used to estimate drying time variance for vessels. The continuous lyophilizer had the shortest difference between the onset and offset times relative to the batch system, indicating that the drying behavior of the vessels was more uniform in the continuous lyophilizer. Variations in drying time were less in the case of continuous freeze-drying relative to batch freeze-drying.

Total Cycle Time

A continuous lyophilizer, as presently disclosed, may allow for a tremendous reduction in drying time. Since there may be no difference in temperature among the vessels during production (that is, during a method described herein), a cycle (also referred to herein as a method) can be designed to maximize efficiency for all vessels. By contrast, in batch freeze-drying, a cycle is often designed using vessels at the edge of the equipment, that might be easily damaged, as reference, making the designed cycle very precautionary for the rest of the batch.

Figure 19:
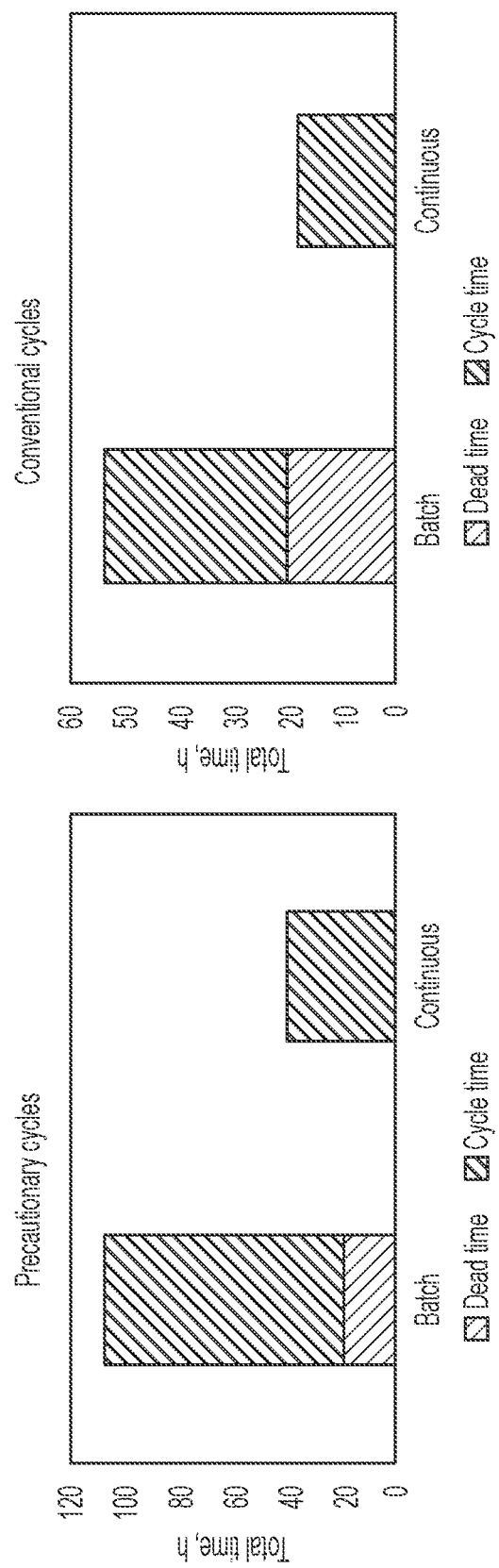
FIG. 19 shows non-limiting illustrative plots comparing total cycle time for batch freeze-drying and continuous freeze-drying in the case of a precautionary cycle (left) and of a more aggressive cycle (right)

FIG. 19 compares the total cycle time for the batch and continuous lyophilizer. The reduction in cycle time by using a continuous lyophilizer can be up to 5 times, and this includes both reduction in drying time and time saved from elimination of all breaks that are typical of the batch system and methods. With constant shelf temperature and pressure, continuous freeze-drying may have between or equal to 3 and 5 times shorter cycle time compared with batch freeze-drying. In addition, continuous freeze-drying may have no dead time, whereas batch freeze-drying may have, e.g., between or equal to 20% and 40% dead time.

Energy Saving

Figure 20:
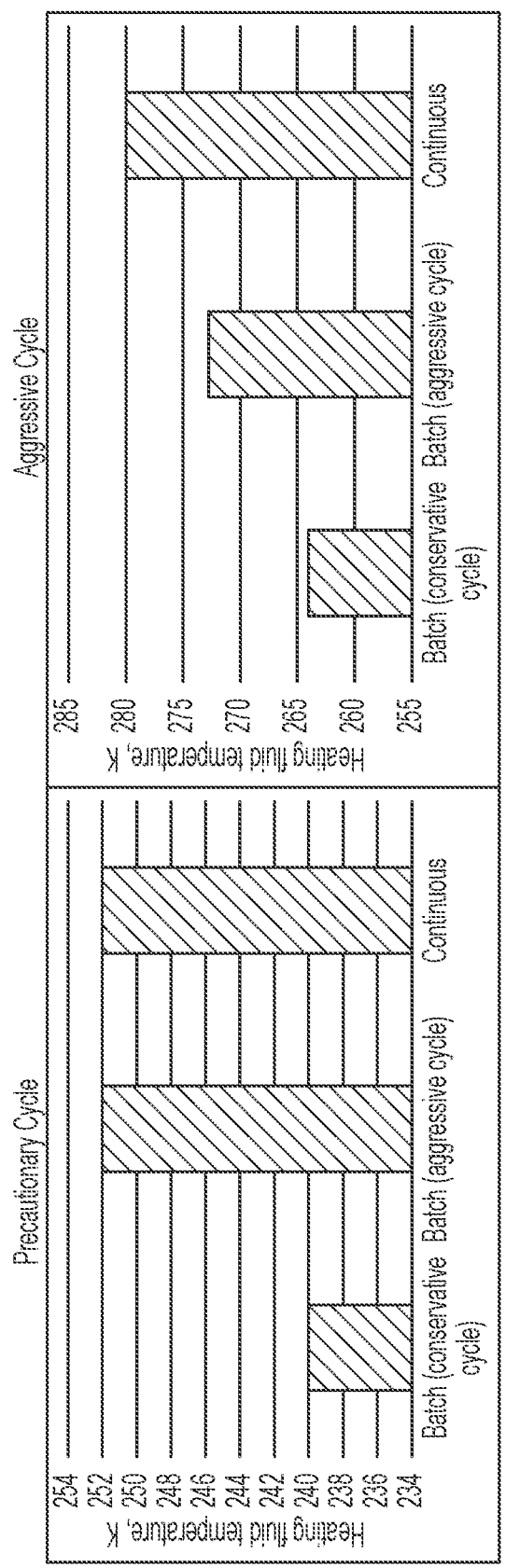
FIG. 20 shows non-limiting illustrative plots comparing the temperature of a heat transfer fluid for a batch freezer-dryer and a continuous freeze-dryer in the case of a precautionary (conservative) batch cycle and a more aggressive batch cycle.

In the presently disclosed process, radiant energy may be used to supply heat to allow sublimation of the solid solvent in a frozen composition being processed (e.g., ice sublimation). This allows the use of a higher temperature of a heat transfer fluid, reducing the energy to be supplied to a refrigeration system and thus enhancing the energy efficiency of the continuous equipment. As an example, FIG. 20 compares the temperature of the heat transfer fluid to be used in a continuous lyophilizer and in a batch lyophilizer to keep the product temperature at a desired value. The comparison is given for a very heat sensitive product (precautionary cycle, left) and a more robust formulation (aggressive cycle, right).

Example 3—Intra-Vessel and Vessel-to-Vessel Heterogeneity

Intra-Vessel Heterogeneity

Figure 21:
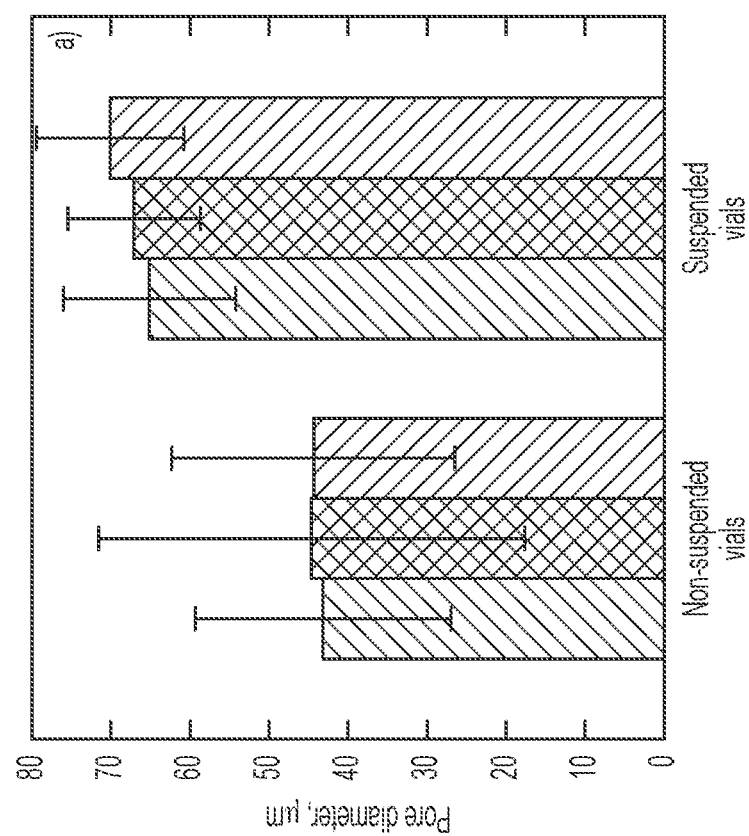
FIG. 21 shows a non-limiting illustrative plot comparing average pore size for three samples produced by a batch lyophilizer (non-suspended vials) and a continuous lyophilizer (suspended vials), wherein error bars refer to size variations along the axial position.

Samples lyophilized by continuous apparatus systematically showed larger pores than those obtained by the batch lyophilizer; see, e.g., FIG. 21. In order to evaluate the impact of a continuous lyophilizer on product uniformity, the internal structure of individual samples was analyzed, by dividing them into three parts: top, center and bottom. Overall, batch freezing led to smaller pores than those obtained by a continuous lyophilizer, approximately 30 microns (vs. preferable 70 microns for continuous lyophilization). Furthermore, samples as obtained by the continuous apparatus were much more uniform (see, e.g., the error bars in FIG. 21).

Figure 22:
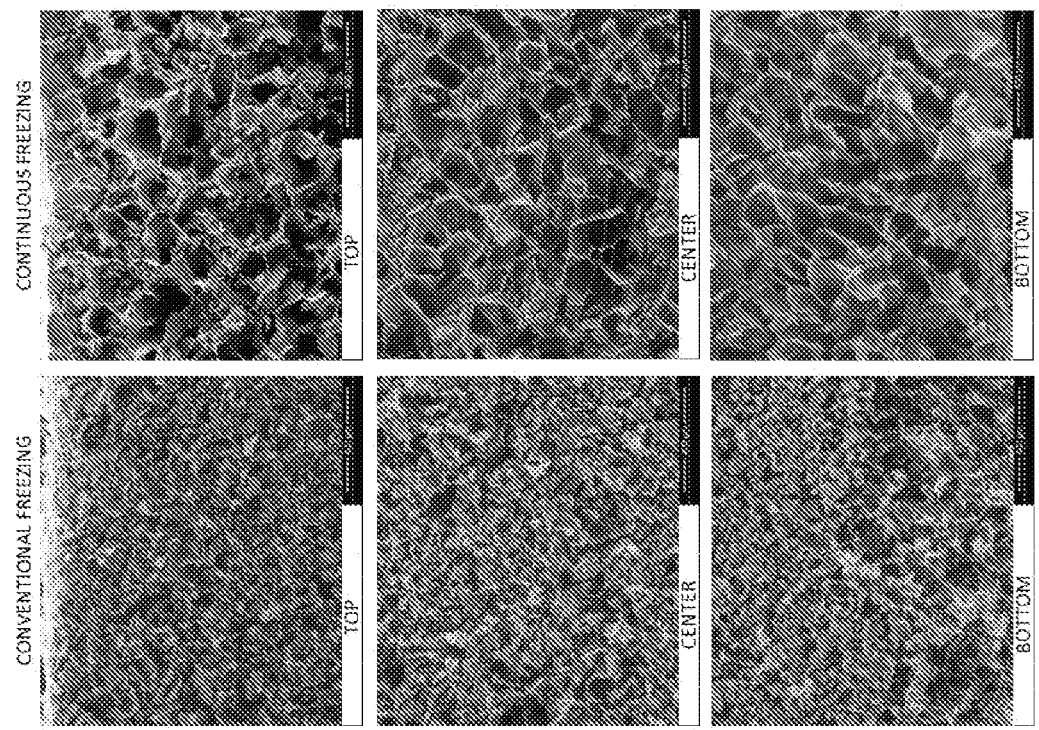
FIG. 22 shows non-limiting scanning electron microscopy (SEM) images of lyophilized samples as produced by a batch apparatus (left images) and a continuous lyophilizer (right images)

In some embodiments, intra-vial heterogeneity in average pore size of a product was reduced by continuous freeze-drying apparatus and methods described herein relative to batch freeze-drying (e.g., FIG. 22). An example of SEM images for the lyophilized samples is given in FIG. 22. FIG. 22 shows scanning electron microscopy images with a scale bar of 400 microns for each image. FIG. 22 demonstrates that intra-vial heterogeneity in pore size was reduced by continuous freeze-drying relative to batch freeze-drying. This may have been at least in part because during a continuous freeze-drying process with suspended vials, heat was more uniformly removed from the liquid composition being frozen, relative to batch freeze-drying with vials directly contacting the base of a chamber.

In certain embodiments, the average pore size of a product resulting from a continuous freeze-drying process including vacuuming-induced surface freezing was 70 microns, whereas a batch process produced a product with an average pore size of 44 microns. In certain embodiments, the average pore size of a product resulting from a continuous freeze-drying process including vacuuming his surface freezing was 40 microns, whereas a batch process produced a product with an average pore size of 20 microns.

Vessel-to-Vessel Heterogeneity

Figure 23:
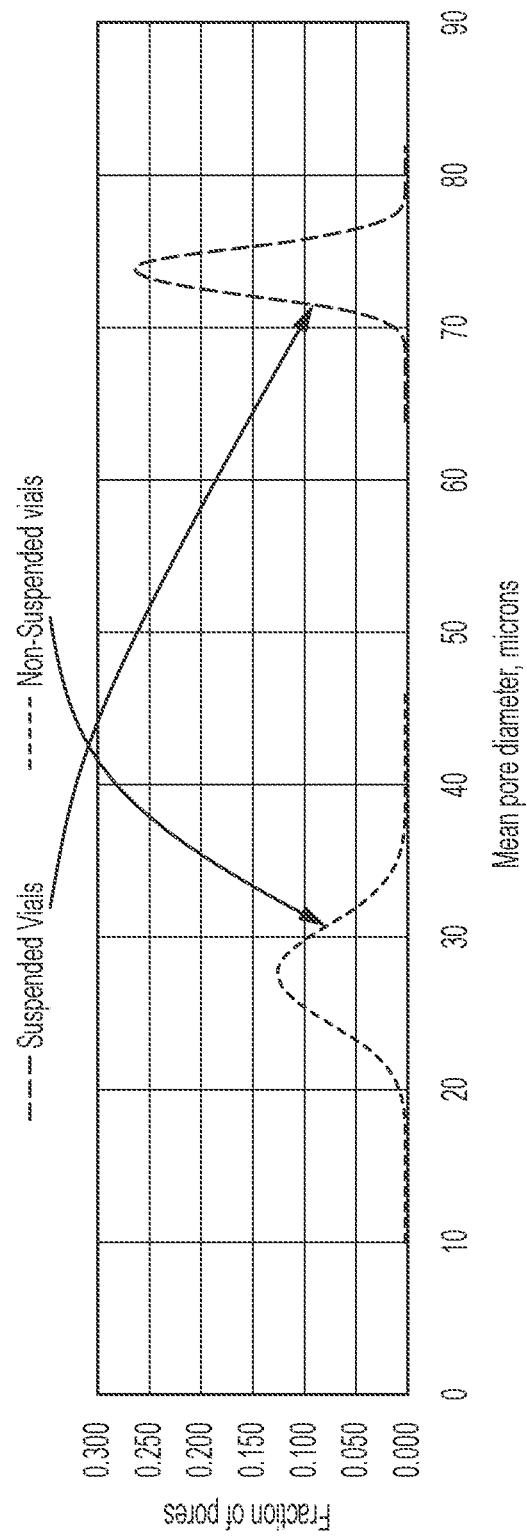
FIG. 23 shows non-limiting statistical distributions of average pore size of lyophilized samples as produced by a batch lyophilizer (left, Non-suspended vials) and a continuous lyophilizer (right, Suspended vials)
Figure 24:
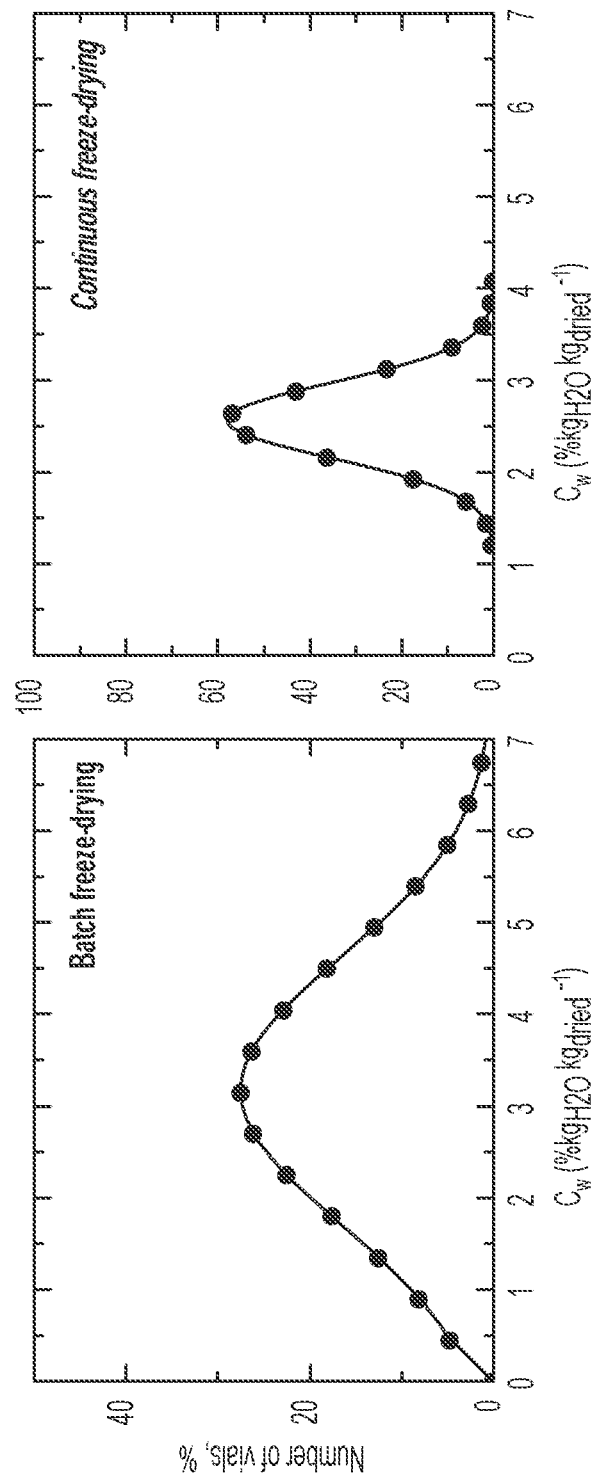
FIG. 24 shows non-limiting statistical distributions of residual moisture as observed at the end of secondary drying in the case of batch freeze-drying and continuous freeze-drying.

As can be seen in FIG. 23, the lot of lyophilized samples produced by a continuous apparatus with suspended vials was much more uniform, in terms of average pore size, than that obtained by a conventional batch lyophilizer with non-suspended vials. It follows that a non-limiting continuous lyophilization system and method reduced vessel-to-vessel heterogeneity and thus enhanced uniformity of the lot. A similar result was also observed in terms of final moisture content $C_w$ (% $kg_{H2O}$ $kg_{dried}^{-1}$, percent kilograms of water ($H_2O$) per kilogram of lyophilized sample (dried)), within a lyophilized sample, which is a parameter that may be controlled to enhance the stability of the active ingredient during storage (see, e.g., FIG. 24). FIG. 24 demonstrates a residual moisture distribution at the end of secondary drying for batch freeze-drying (left) and continuous freeze-drying (right). Heterogeneity in residual moisture was reduced for continuous freeze-drying relative to batch freeze-drying. Therefore, in some embodiments, continuous freeze-drying systems and methods herein provided increased stability of an active ingredient during storage relative to batch freeze-drying.

Example 4—Flexibility/Modularity

Figure 25:
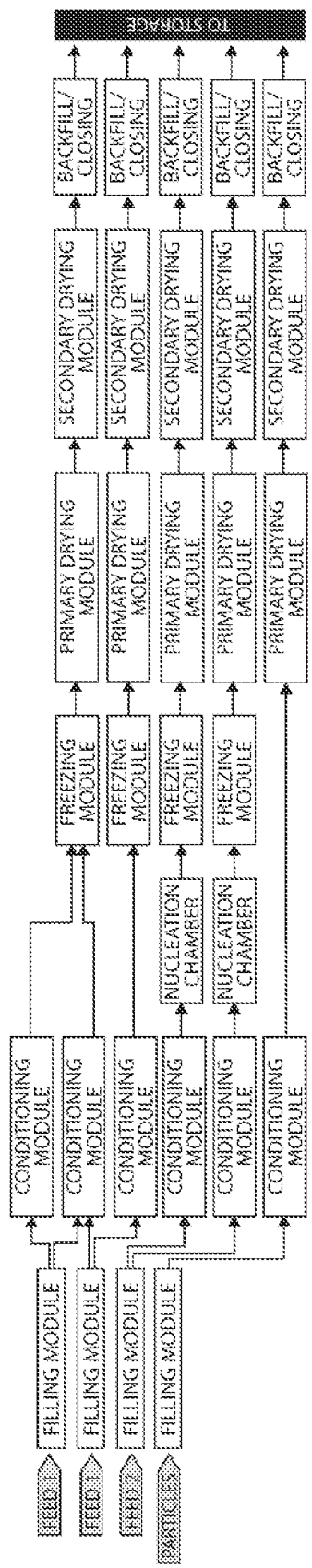
FIG. 25 depicts a non-limiting example of potential configurations for a continuous lyophilizer.

Systems and methods disclosed herein use different modules in some embodiments, each of which are specialized to a single operation. These modules can be combined in order to produce products from different upstream feeds and, eventually, in different form or with different characteristics, as depicted e.g. in FIG. 25, making this technology very flexible. As shown in FIG. 25, in some embodiments, modularity is provided and modules can work in parallel, depending for example on the desired productivity of the system (e.g., number of vials per week). The modularity of the system may also allow for synchronization of processing time and therefore speed of travel of vessels through the various modules.

Example 5—Equipment Size

FIG. 26 compares equipment size of a batch lyophilizer and a continuous lyophilizer in the case of two non-limiting case studies, which were characterized by different yields. In some case studies with 200,000 vials per week, in the case of continuous freeze-drying, the chamber volume was up to 12 times smaller than that of a batch unit. In some case studies with 100,000 vials per week, in the case of continuous freeze-drying, the chamber volume was up to 15 times smaller than that of a batch unit. The continuous lyophilizer allowed a reduction in equipment size by up to 15 times for a given yield.

The size of a given module (e.g., chamber) may be customizable depending on the desired productivity. Module size can be designed based upon, for example, a) residence time, b) speed of travel, and c) dimensions of the channel in the chamber. a) Residence time may be product-specific, and depends for example on the drying time. b) Once the dimensions of a module are fixed, a speed of travel may be determined in order to obtain a certain residence time for a vial in the module. c) The dimensions of a channel (e.g., in a module) may depend for example on the type of vessels used in the process and vessel size. An example of a calculation for a drying chamber is included in Table 2.

TABLE 2

| Quantity | Value | Method of Determination |
|---|---|---|
| Residence time | 30 h | Determined by a process |
| Channel dimension | 0.05 m by 0.03 m | Determined by vial type |
| Total length of the path | 35 m | Designed |
| Dimension of the chamber | Length 1.82 m<br>Height 0.07 m<br>Width 3.00 m | |
| Speed of travel | 1.2 m/h | Determined from the total length of a path and residence time |
| Productivity | 49 vials/h | |

Example 6—Connections Between Modules

Figure 28:
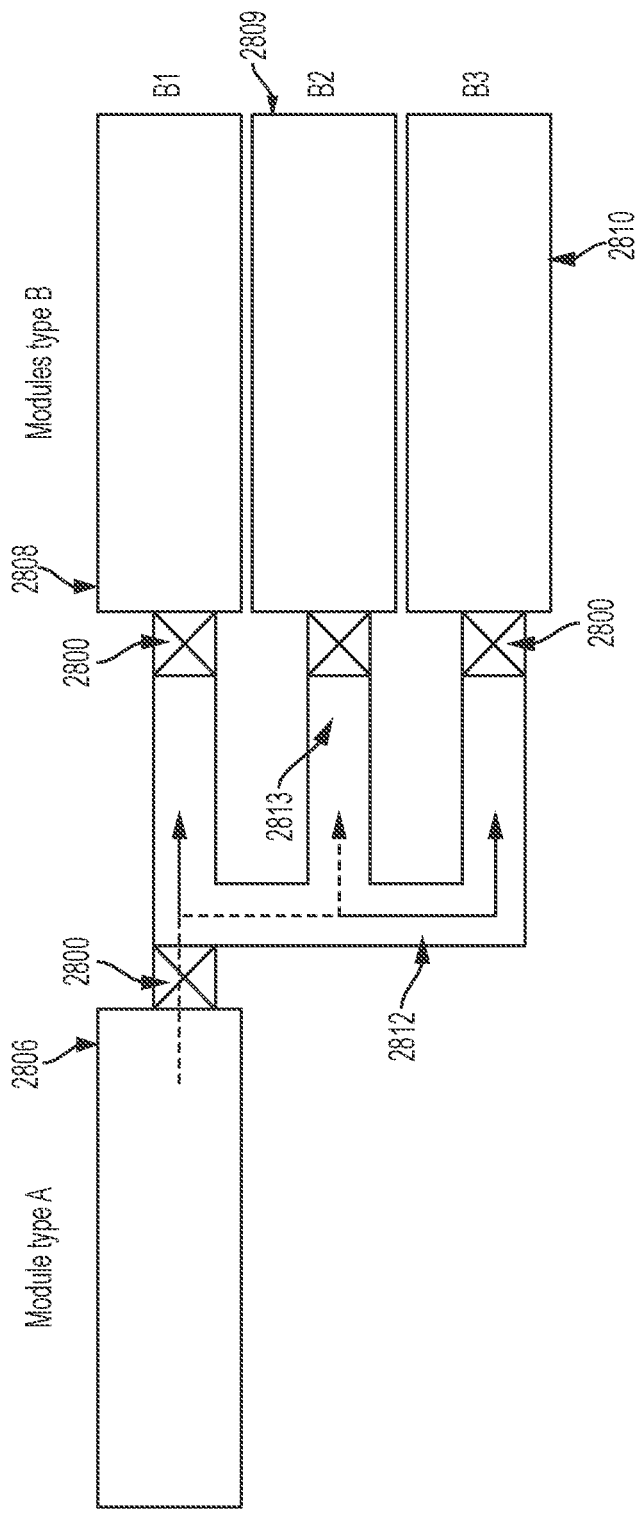
FIG. 28 shows a non-limiting schematic diagram of an illustrative network pipe system to connect modules, wherein Module type A and Module type B are modules that have different functionality.

Each module in a system for continuous freeze-drying may be dedicated to one process step and may be connected with the other modules through small pipes. The length of these pipes may depend on the dimension of the whole lyophilizer and on the number of modules. To achieve flexibility of use, when a vial reaches the end of a module, it can be sent to one of a selection of other modules, as shown in FIG. 28. FIG. 28 shows a non-limiting network pipe system to connect modules, wherein Module type A (2806) and Module type B (2808, 2809, or 2810) are modules that have different functionality. At the end and at the beginning of each module, there may be an interface apparatus (2800, e.g., a valve, a gate system, a load-lock system) connecting the module 2806 with other module(s) 2808, 2809, and/or 2810. In some embodiments, an automatic selector system sends each vial along a correct path that has been dedicated for that production method in order to reach a respective next module. For example, once a vial exits module type A (2806, e.g., a freezing module) it follows a specific path to reach one of the modules type B (2808, 2809, or 2810, e.g., primary drying modules). For example, a vial may move from Module type A (2806) to Module type B2 (2809). The pipe network system 2812 may be essentially confined within a box that allows control to a desired temperature. For example, if vials move from a module type A (2806, e.g., primary drying module) to module type B2 (2809, e.g., a secondary drying module), pressure within connecting pipe 2813 is regulated according to the conditions of module type B2 (2809). This system imparts advantages of high modularity and flexibility.

Figure 29:
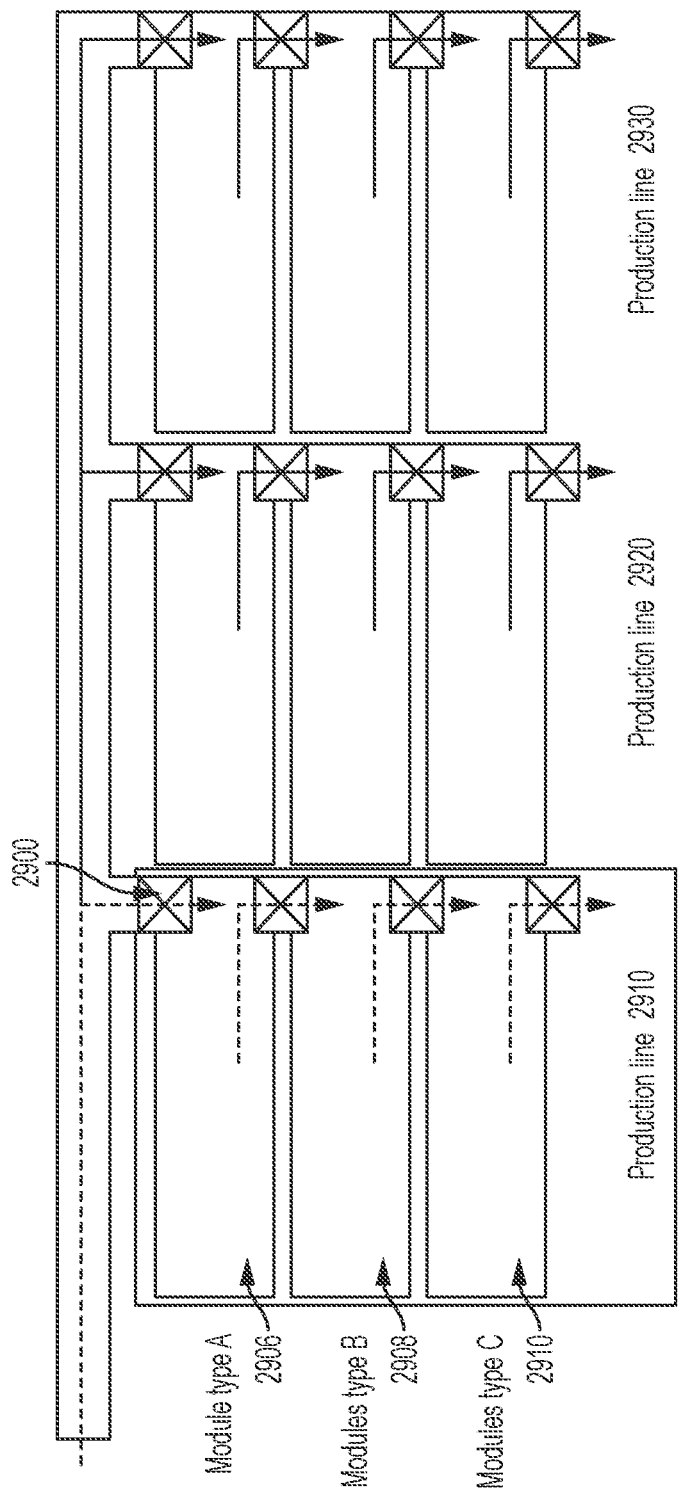
FIG. 29 provides a non-limiting schematic diagram of an illustrative stack module system wherein Module type A, Module type B, and Module type C are modules that have different functionality.

In some embodiments, an alternative to this configuration involves stacking modules with different functionality. In such cases, it is possible to work with predefined lines of production that are dedicated to a certain process or product. FIG. 29 provides a non-limiting schematic diagram of a stack module system wherein Module type A (2906), Module type B (2908), and Module type C (2910) are modules that have different functionality. At the inlet and outlet of each module, there is an interface apparatus (2900, e.g., a valve, a gate system, a load-lock system) connecting the module with other module(s). For example, vials may be processed in production line 2910, as in the schematic diagram. This system imparts advantages of ease of design and ease of management during production.

Example 7

Figure 32:
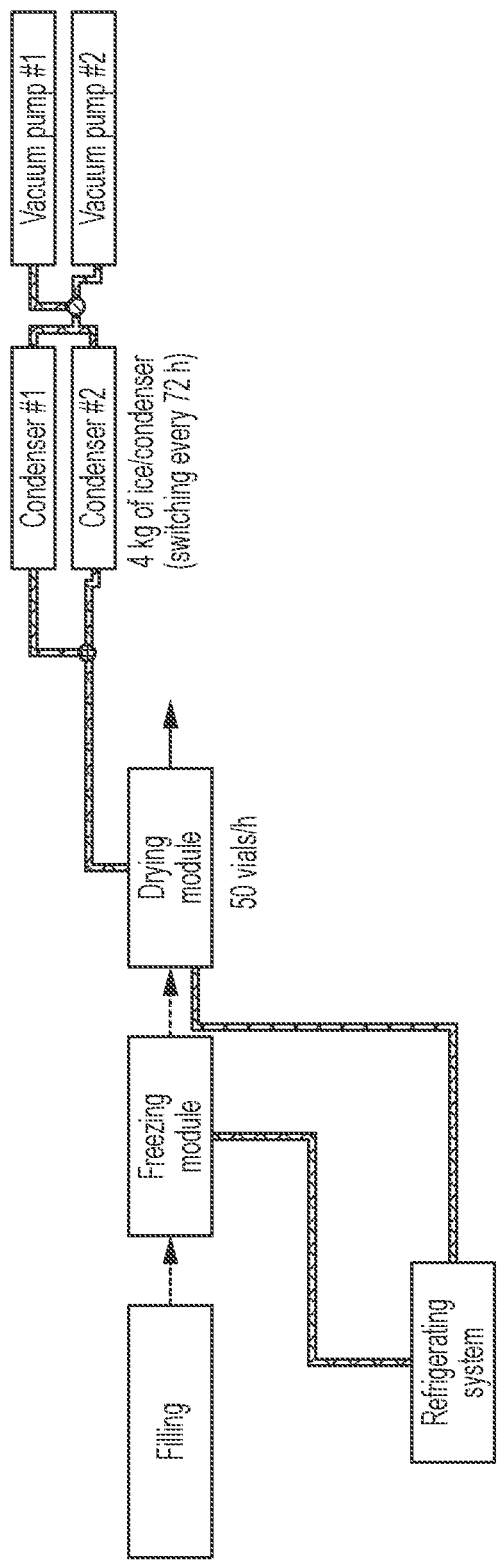
FIG. 32 is a non-limiting schematic of an apparatus for freeze-drying a composition.

FIG. 32 is a schematic of an apparatus for freeze-drying a composition, in accordance with some illustrative embodiments. The apparatus may comprise a filling module connected to a freezing module which is in turn connected to a drying module. Both the freezing module and the drying module may be connected to a refrigeration module, and the drying module may be connected to two condensers which are in turn connected to vacuum pumps. The drying module may be operated under conditions so as to produce 50 vials per hour. Each condenser may consume 4 kg of ice per 72 hours.

Example 8

Figure 33:
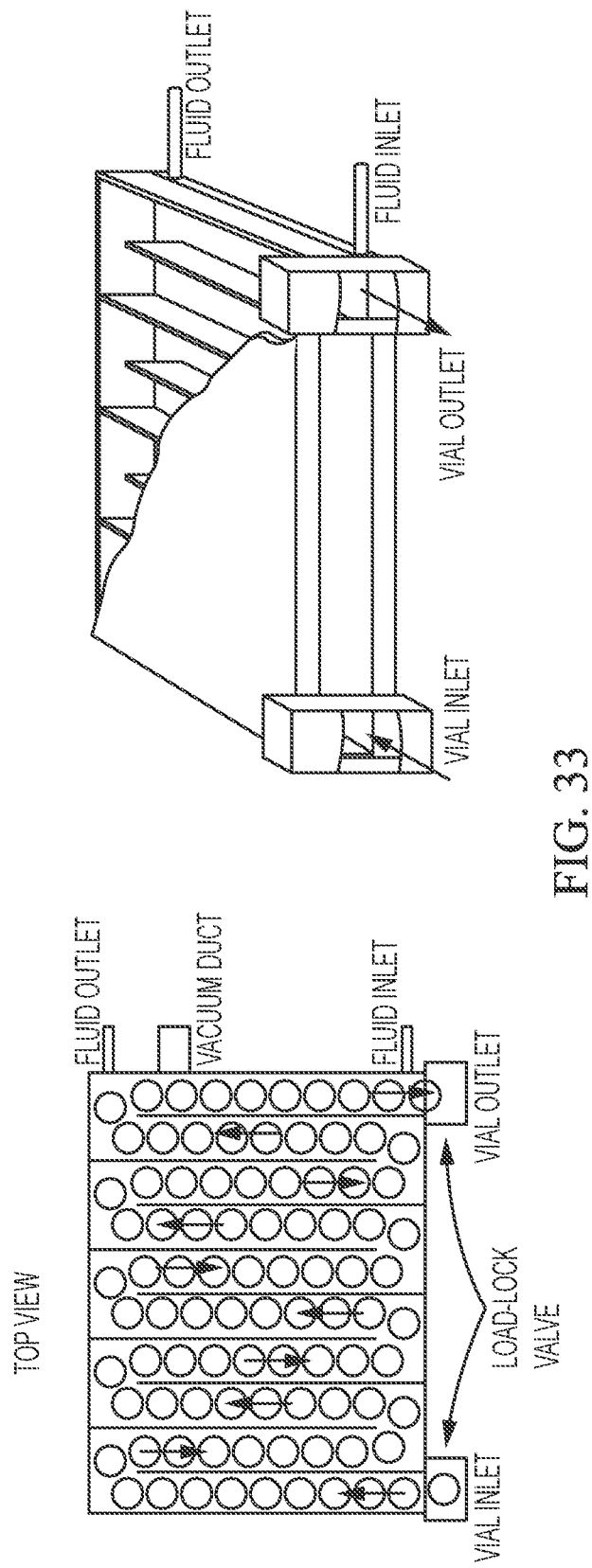
FIG. 33 shows non-limiting schematics of a freezing module or a drying module.

FIG. 33 is a schematic of a top view of a drying module (left), and a perspective view of a freezing module or a drying module (right), in accordance with some illustrative embodiments. The freezing module or drying module may have a serpentine path for vials to travel through. At the vial inlet and the vial outlet may be located a respective load-lock system (also referred to herein as a load-lock valve) to accommodate a difference in pressure between the freezing module or drying module and another module in the apparatus from which or to which a vial is traveling.

Example 9

Figure 34:
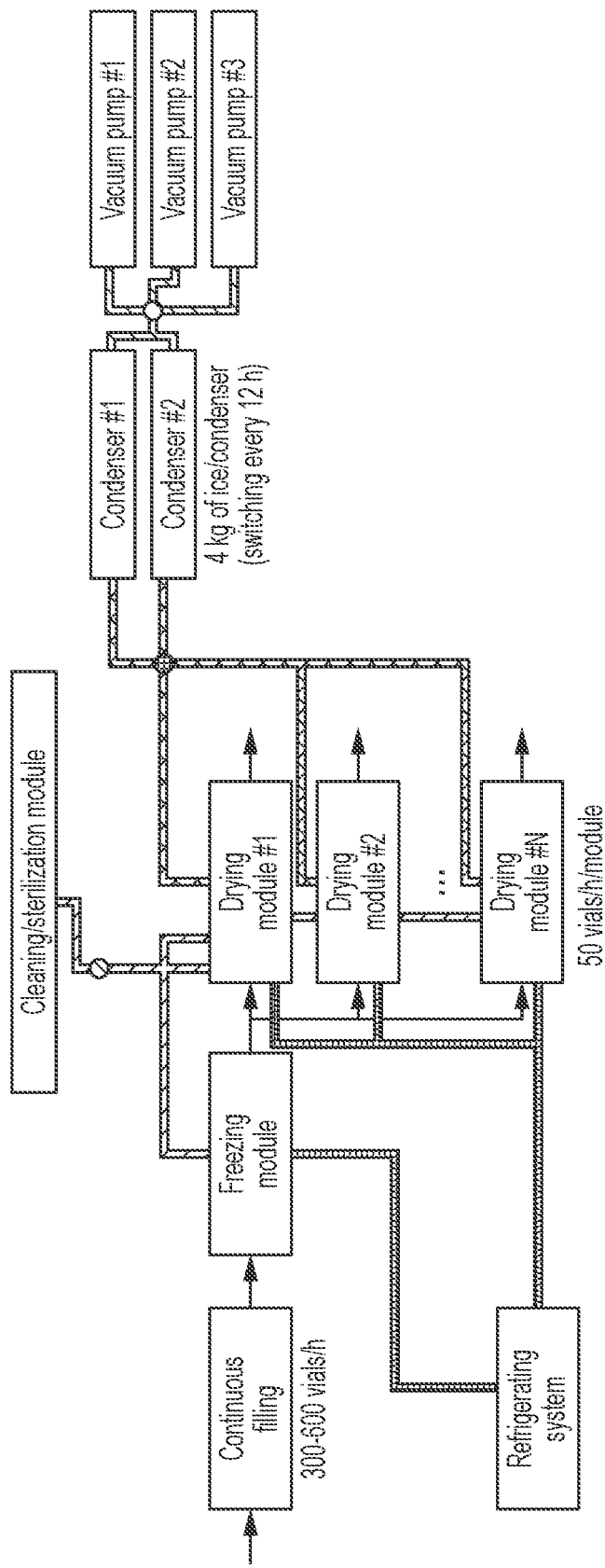
FIG. 34 is a non-limiting schematic of an apparatus for freeze-drying a composition.

FIG. 34 is a schematic of an apparatus for freeze-drying a composition, in accordance with some illustrative embodiments. The apparatus may comprise a continuous filling module connected to a freezing module, which is in turn connected to a plurality of drying modules. A refrigeration module may be connected to both the freezing module and each of the plurality of drying modules. A cleaning/sterilization module may be connected to both the freezing module and each of the plurality of drying modules. Three vacuum pumps may be connected to two condensers, which in turn may be connected to each of the drying modules Example 10

Figure 35:
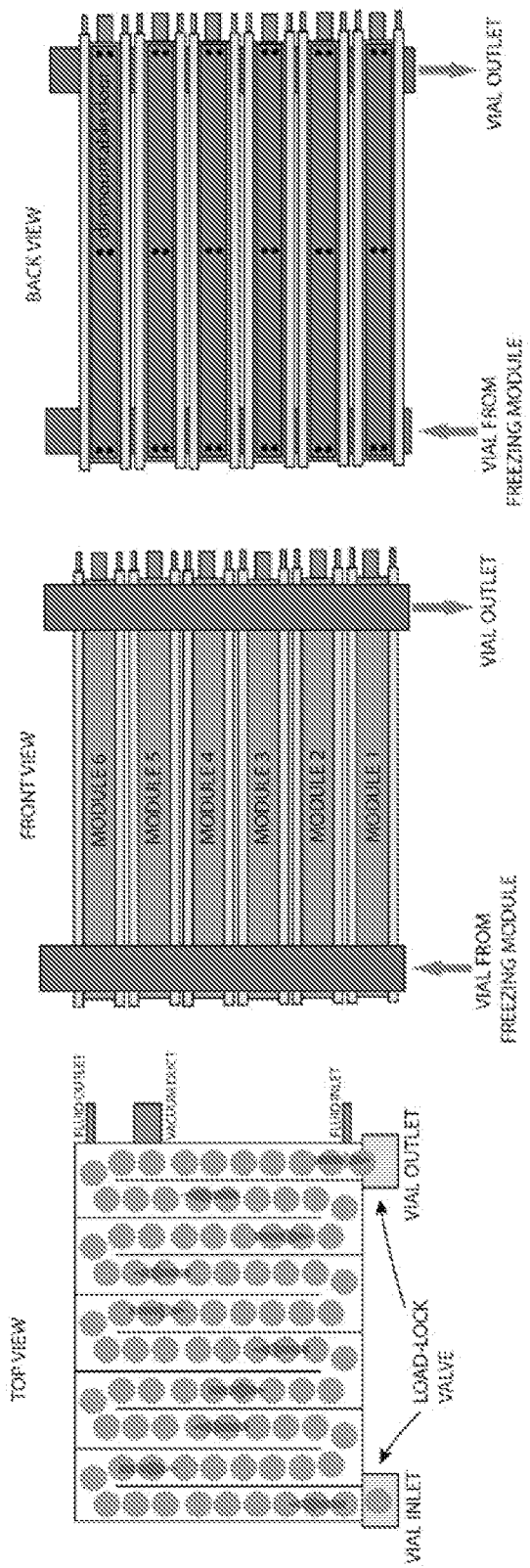
FIG. 35 shows non-limiting schematics of drying modules.

FIG. 35 is a schematic of a top view of a drying module (left), and a front view (center) and back view (right) of a parallel stack of drying modules, in accordance with some illustrative embodiments. The drying modules may be accommodating vials that move in parallel, each vial entering a drying module from a common freezing module. Each of the drying modules may include a dismountable door.

Example 11

Figure 36:
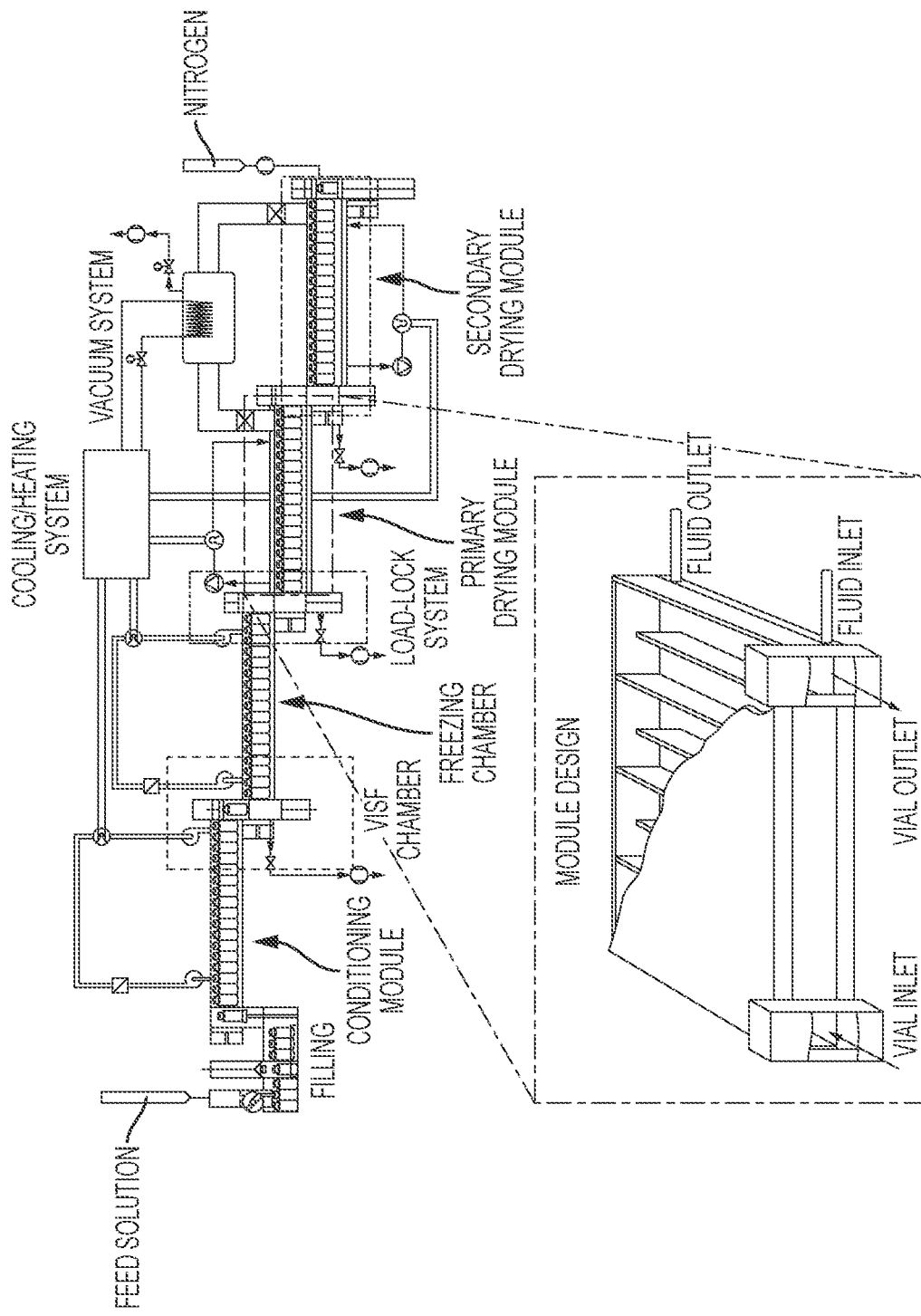
FIG. 36 shows a non-limiting apparatus for freeze-drying compositions contained in vessels.

FIG. 36 shows a system for freeze-drying compositions contained in vials, in accordance with some illustrative embodiments.

A method of operating a system, for freeze-drying compositions contained in vials, may begin with continuously filling vials with a fluid composition to be freeze-dried, which vials are suspended over a moving track before or after filling. The vials may then be moved into a conditioning module. In the conditioning module, the flow of a cryogenic gas may cool down the vial, bringing the composition to the desired temperature. At the end of the conditioning module, the vial may move into a nucleation chamber, also referred to as a vacuum induced surface freezing (VISF) chamber, where the pressure is low enough to induce nucleation of solid crystals of the composition.

Following the nucleation chamber, the vial may move into a freezing module, where, again, a cryogenic gas cools down the vial, achieving complete solidification of the composition. It may be possible to create customizable freezing protocols by changing the gas velocity, and so, modulating the freezing rate. The vial may then be transferred to a drying module by means of a load-lock system, which facilitates the passage of the vial from a module at a higher pressure to another module at lower pressure without breaking the vacuum. In the drying module, vials may be suspended over a track and move in the module following a serpentine path. A freezing module and/or a drying module may comprise temperature-controlled walls that supply heat to the product via radiation. By changing the temperature of the walls of a module in which a composition resides, it may be possible to modulate heat transferred to the composition, and, hence, to carry out both gentle and aggressive cycles. The last step of a method provided herein may comprise backfilling and vial stoppering. An entire method herein may be carried out continuously, without breaks or manual intervention between steps or modules.

This non-limiting system and associated methods may result in increased control of product structure, which can be facilitated by VISF, and increased control and uniformity of heat supplied to the composition during drying. By using VISF, nucleation temperature may be approximately the same for every sample of a composition, minimizing or eliminating differences in freezing history of the product, and, thus, minimizing or eliminating differences in final product structure for different vials. This technique may facilitate production of freeze-dried products with desired morphological attributes by changing cooling rate after nucleation has occurred.

In addition, contrary to batch lyophilization, small variations in geometry of the vials used in continuous freeze-drying methods herein with suspended vials may have no significant effect on the heat supplied by radiation. Heat by radiation may be independent of chamber pressure, facilitating further reduction of pressure and therefore increased sublimation rate from the composition.

Non-limiting methods herein produced very uniform products, with approximately the same characteristics as one another in different vials, because each vial underwent approximately the same process conditions. Non-limiting methods provided herein may also be used to process particle-based materials in vessels, and may employ any shape of vessel for containing a composition to be freeze-dried. In some experiments, drying duration was shortened by between or equal to 2 and 4 times, and total freeze-drying cycle duration was shortened by up to 10 times, at least because dead time was eliminated.

In some embodiments of the current disclosure, processing time and equipment footprint were dramatically reduced, no manual operation or breaks were necessary, in-line control was implemented, and scale-up is straightforward and involves adding parallel modules.

Non-limiting systems and methods herein involve VISF protocols, but can also be extended to particle-based products in vessels. Using VISF, product structure may be well-controlled, and methods herein can be designed to modulate the freezing rate of a composition.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A system for processing a composition, the system comprising:
    a plurality of modules arranged to promote step-wise freezing and drying of a composition, the plurality of modules comprising:
        a conditioning module;
        a freezing module; and
        a drying module; and
    a conveyer system configured to move a vessel configured to contain the composition through the plurality of modules, wherein the conditioning module is configured to bring the composition to a conditioning temperature prior to freezing, and
    wherein the vessel comprises a housing defining a boundary between an exterior surrounding of the vessel and an interior space configured to contain the composition, and wherein, when present in a module of the plurality of modules, the vessel is arranged to promote heat transfer between the exterior surrounding and the interior space across an entire portion of the housing contactable with the composition in the interior space when the composition is present in the interior space.

2. The system of claim 1, further comprising one or more control systems configured to control one or more processing conditions.

3. The system of claim 1, further comprising one or more cleaning/sterilization modules configured to sterilize one or more modules while a respective module does not contain a vessel containing the composition.

4. The system of claim 1, wherein the plurality of modules occupies a total volume of between or equal to 0.1 $m^3$ and 4 $m^3$.

5. The system of claim 1, wherein the drying module is connected to the freezing module by an interface apparatus.

6. The system of claim 1, wherein the freezing module includes one freezing module and the drying module includes 6 drying modules, wherein the 6 drying modules are configured to operate in parallel and each of the 6 drying modules is connected to the freezing module by a respective interface apparatus.

7. The system of claim 1, wherein the plurality of modules comprises a filling module.

8. The system of claim 1, wherein the plurality of modules comprises a nucleation module, wherein the conveyor system is configured to move the vessel from the conditioning module to the nucleation module.

9. The system of claim 1, further comprising a refrigeration system.

10. The system of claim 1, further comprising a vacuum system.

11. The system of claim 1, further comprising a load-lock system located at a vessel outlet of a first module and a vessel inlet of a second module configured to accommodate a change in pressure between the first module and the second module.

12. The system of claim 1, wherein the composition comprises a pharmaceutical.

13. The system of claim 1, wherein the composition comprises an excipient.

14. The system of claim 1, wherein the composition comprises fruit pulp, juices or another liquid mixture.

15. The system of claim 1, wherein a volume of a given module is fifteen times less than that of a freezing and/or drying chamber used in a reference batch process.

16. A method for processing a composition, the method comprising:
    moving a plurality of vessels along a common path through each module of a plurality of modules arranged to promote step-wise freezing and drying of the composition, wherein each vessel is configured to contain the composition, wherein each vessel comprises a housing defining a boundary between an exterior surrounding of the vessel and an interior space configured to contain the composition, and wherein the plurality of modules comprises a conditioning module, a freezing module, and a drying module; and
    cooling the composition in each vessel to a conditioning temperature in the conditioning module prior to freezing.

* * * * *